US011432941B2

(12) United States Patent
Biedermann et al.

(10) Patent No.: US 11,432,941 B2
(45) Date of Patent: Sep. 6, 2022

(54) INTERVERTEBRAL IMPLANT AND SYSTEM OF AN INTERVERTEBRAL IMPLANT AND AN INSTRUMENT FOR INSERTING THE INTERVERTEBRAL IMPLANT

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Achim Zipse, Baden-Baden (DE); Gael Dreher, Karlsruhe (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 147 days.

(21) Appl. No.: 15/178,534

(22) Filed: Jun. 9, 2016

(65) Prior Publication Data

US 2016/0361177 A1 Dec. 15, 2016

Related U.S. Application Data

(60) Provisional application No. 62/173,858, filed on Jun. 10, 2015.

(30) Foreign Application Priority Data

Jun. 10, 2015 (EP) ..................... 15171529

(51) Int. Cl.
*A61F 2/44* (2006.01)
*A61F 2/46* (2006.01)
*A61F 2/30* (2006.01)

(52) U.S. Cl.
CPC ............ *A61F 2/4465* (2013.01); *A61F 2/442* (2013.01); *A61F 2/446* (2013.01); *A61F 2/4455* (2013.01);
(Continued)

(58) Field of Classification Search
CPC ........ A61F 2/442; A61F 2/4425; A61F 2/446; A61F 2/4465; A61F 2/447; A61F 2/4611;
(Continued)

(56) References Cited

U.S. PATENT DOCUMENTS 5,709,683 A * 1/1998 Bagby ...................... A61F 2/44
623/17.11
6,007,544 A * 12/1999 Kim ............... A61B 17/320016
606/108
(Continued)

FOREIGN PATENT DOCUMENTS

CN 1819805 A 8/2006
CN 1822804 A 8/2006
(Continued)

OTHER PUBLICATIONS

Extended European Search Report for corresponding European Application No. 15171529.9 in the name of Biedermann Technologies GmbH & Co. KG, European Search Report dated Jan. 6, 2016 and dated Jan. 14, 2016 (6 pgs).

*Primary Examiner* — Kevin T Truong
*Assistant Examiner* — Tracy L Kamikawa
(74) *Attorney, Agent, or Firm* — Lewis Roca Rothgerber Christie LLP

(57) ABSTRACT

An intervertebral implant includes: a body with an upper wall configured to engage a first vertebral end plate and a lower wall configured to engage a second vertebral end plate, and a load transmitting part configured to transmit load between the upper wall and the lower wall; and the load transmitting part is configured to assume a compressed condition in which a distance between the upper wall and the lower wall defines a first height of the implant and an expanded condition in which the distance between the upper wall and the lower wall defines a second height of the implant that is greater than the first height; and the load
(Continued)

transmitting part is attached to the upper wall at at least two first connecting locations and is attached to the lower wall at at least two second connecting locations and has substantially an X-shape in a front view of the implant; and the implant is made of a material that exhibits shape memory properties that permit the implant to remain in the compressed condition without outside forces acting upon it and to change to the expanded condition in response to a temperature being directed to a recovery level.

24 Claims, 28 Drawing Sheets

(52) U.S. Cl.
CPC ... *A61F 2/4611* (2013.01); *A61F 2002/30092* (2013.01); *A61F 2002/30116* (2013.01); *A61F 2002/30118* (2013.01); *A61F 2002/30179* (2013.01); *A61F 2002/30538* (2013.01); *A61F 2002/30556* (2013.01); *A61F 2002/30593* (2013.01); *A61F 2002/30622* (2013.01); *A61F 2002/30677* (2013.01); *A61F 2002/30772* (2013.01); *A61F 2002/30836* (2013.01); *A61F 2002/30904* (2013.01); *A61F 2002/4615* (2013.01); *A61F 2002/4622* (2013.01); *A61F 2002/4627* (2013.01); *A61F 2002/4629* (2013.01)

(58) Field of Classification Search
CPC ........ A61F 2002/443; A61F 2002/4475; A61F 2002/4615; A61F 2002/4622; A61F 2002/4629; A61F 2002/30092; A61F 2002/30179; A61F 2/44
USPC ............................................ 623/17.11–17.16
See application file for complete search history.

(56) References Cited

U.S. PATENT DOCUMENTS

| | | | |
|---|---|---|---|
| 6,758,863 B2* | 7/2004 | Estes | A61F 2/442 623/17.16 |
| 7,537,616 B1* | 5/2009 | Branch | A61F 2/4603 623/17.11 |
| 2004/0010315 A1 | 1/2004 | Song | |
| 2004/0254520 A1* | 12/2004 | Porteous | A61F 9/00781 604/8 |
| 2005/0015095 A1 | 1/2005 | Keller | |
| 2005/0203626 A1 | 9/2005 | Sears et al. | |
| 2006/0142860 A1 | 6/2006 | Navarro et al. | |
| 2006/0149273 A1 | 7/2006 | Ross et al. | |
| 2006/0229724 A1 | 10/2006 | Lechmann et al. | |
| 2006/0247771 A1 | 11/2006 | Peterman et al. | |
| 2007/0225812 A1 | 9/2007 | Gill | |
| 2008/0114454 A1* | 5/2008 | Peterman | A61F 2/44 623/17.16 |
| 2008/0167686 A1* | 7/2008 | Trieu | A61F 2/442 606/249 |
| 2008/0228276 A1 | 9/2008 | Mathews et al. | |
| 2009/0054987 A1* | 2/2009 | Chin | A61F 2/447 623/17.11 |
| 2009/0182429 A1 | 7/2009 | Humphreys et al. | |
| 2010/0023019 A1 | 1/2010 | Fuhrer et al. | |
| 2011/0106263 A1 | 5/2011 | Eisermann et al. | |
| 2012/0065681 A1 | 3/2012 | DiLorenzo | |
| 2012/0078313 A1 | 3/2012 | Hasse et al. | |
| 2013/0006362 A1 | 1/2013 | Biedermann et al. | |
| 2013/0166030 A1* | 6/2013 | Biedermann | A61F 2/4611 623/17.16 |
| 2013/0304213 A1 | 11/2013 | Aflatoon et al. | |
| 2014/0249636 A1 | 9/2014 | Bouchot et al. | |
| 2016/0324653 A1* | 11/2016 | Flickinger | A61F 2/30771 |

FOREIGN PATENT DOCUMENTS

| | | |
|---|---|---|
| CN | 1893896 A | 1/2007 |
| CN | 101111208 A | 1/2008 |
| CN | 101573090 A | 11/2009 |
| CN | 101969888 A | 2/2011 |
| CN | 102824233 A | 12/2012 |
| CN | 103118637 A | 5/2013 |
| CN | 103169552 A | 6/2013 |
| CN | 104010596 A | 8/2014 |
| CN | 104146754 A | 11/2014 |
| CN | 104546230 A | 4/2015 |
| JP | 2008-539016 A | 11/2008 |
| JP | 2013-132557 A | 7/2013 |
| WO | WO 01/01895 A1 | 1/2001 |
| WO | WO 2007/095333 A2 | 8/2007 |
| WO | WO 2008/022206 A2 | 2/2008 |
| WO | WO 2012/039865 A1 | 3/2012 |

* cited by examiner INTERVERTEBRAL IMPLANT AND SYSTEM OF AN INTERVERTEBRAL IMPLANT AND AN INSTRUMENT FOR INSERTING THE INTERVERTEBRAL IMPLANT

CROSS-REFERENCE TO RELATED APPLICATIONS

This application claims the benefit of U.S. Provisional Patent Application Ser. No. 62/173,858, filed on Jun. 10, 2015, and also claims priority to European Patent Application No. 15 171 529.9, filed on Jun. 10, 2015, the entire content of each of which is hereby incorporated by reference.

BACKGROUND

The invention relates to an intervertebral implant and to a system of such an intervertebral implant and an instrument for inserting the same. The intervertebral implant comprises a body with an upper wall configured to engage a first vertebral end plate and a lower wall configured to engage a second vertebral end plate, and a load transmitting part configured to transmit load between the upper wall and the lower wall, wherein the load transmitting part is configured to assume a compressed condition in which the implant has a first height and an expanded condition in which the implant has a second height greater than the first height and wherein the implant is made of a material with shape memory properties. An instrument is configured to be attached to the implant and to hold the implant in the compressed condition without exerting external forces to maintain it in the compressed condition.

An intervertebral implant of this type is known from US 201310166030 A1. The intervertebral implant comprises a load transmitting part with at least one strut having a first end formed monolithically with the upper wall or the lower wall and a second end that is free.

US 2008/0167686 A1 describes an intervertebral spacer including a non-rigid body having an upper beam member and a lower beam member. An upper inner surface of the lower beam member and a lower surface of the upper beam member may define an oval-shaped hollow portion. The spacer may also include a support member that extends from one portion of an inner sidewall to another portion of the inner sidewall within the hollow portion. In one embodiment, the support member attaches to the inner sidewall at four locations and forms an X shape within the hollow portion dividing the hollow portion into four regions. The spacer may be made of a nickel titanium alloy.

SUMMARY

According to an aspect of embodiments of the invention, an intervertebral implant permits a simplified insertion and a gentle expansion of the intervertebral space while providing simultaneously a good fusion. Further, an instrument adapted to insert the intervertebral implant and a system of an intervertebral implant and an instrument shall be provided.

Aspects and features of embodiments of the invention are described herein with respect to some exemplary embodiments and are set forth in the claims.

The intervertebral implant can be inserted into the intervertebral space in a compressed condition without exerting external compression forces to maintain the implant in the compressed condition. Optionally, the implant can be compressed also in the width direction. After insertion, the implant is self-expanding, i.e. it assumes the expanded condition only by the influence of body heat of the patient. Thereby, the distance between two adjacent vertebrae is gently enlarged to a predetermined distance defined by the height differences of the implant in the expanded and the compressed condition. The implant may be compressed to have about 25% or more reduction in height. A geometry of the implant in the expanded condition is defined by a memorized shape of the implant that can be assumed by directing the temperature towards a recovery level above which the shape memory material changes its structure. Such a recovery level may be the $A_f$ temperature for a nickel titanium alloy that may be preferably between about 20° C. to about 35° C. and more preferably between about 25° C. and about 30° C. such that the implant can expand under the influence of body heat. The properties of the implant can be obtained by selecting the chemical composition of the material and/or the treatment of the material.

The implant is a monolithic body. A load transmitting part is provided that has in a front view an X-shape. Hence, the supporting main structure is provided substantially in the middle of the implant between the upper wall and the lower wall. By the X-shape, two arms that are connected to the upper wall and two legs that are connected to the lower wall are provided wherein the arms and the legs are connected together at a location between the upper wall and the lower wall. An angle between the arms may be greater than an angle between one arm and one leg. A thickness of the arms and/or the legs of the load transmitting part may be increased at or near the connecting locations to the upper and/or lower wall. Such enhanced thickness prolongs the lifetime of the implant under cyclic loads.

The upper and lower wall may be substantially parallel to each other or may be inclined with respect to each other. In the case of inclined upper and lower walls, the implant may be used, for example, in the region of the lumbar spine in a case of normal lordosis or for correcting an abnormal lordosis. Moreover, the upper and/or the lower wall may be substantially flat.

The outer contour of the implant in a top view may be straight to be suitable for an XLIF procedure or banana-shaped to be suitable for a TLIF procedure. Additionally, sidewalls may be provided for facilitating the insertion and/or increasing the torsional stiffness. Such sidewalls may narrow towards the outer ends to provide a reduced width at the outer ends for easier insertion. Moreover, the sidewalls may provide features for the attachment of an instrument. Optionally, the sidewalls may have an opening for filling in bone graft after insertion of the implant.

For better fixation to the end plates of the vertebral bodies, a plurality of bone engagement projections or teeth may be provided on the upper wall and/or the lower wall. The teeth may be provided only in the area of the load transmitting part. In a side view, an area of the upper wall or the lower wall where the teeth are provided may be flat. The teeth may be provided in rows and a height of the teeth may decrease towards the end of the row. This facilitates the insertion of the implant. Moreover, this design permits a better adaptation to the vertebral body. The teeth may be positioned below a highest profile in a side view of the implant in the compressed condition. By means of this, the teeth do not form an obstacle during insertion. In a particular design, the teeth may have a keel-like shape extending substantially in the direction of insertion of the implant. This provides guidance in a case where the end plates of the vertebral bodies are contacted during insertion. The keel-like shape also prevents displacement after insertion of the intervertebral implant.

A stiffness of the implant is slightly reduced due to the material that may exhibit superelastic properties in the expanded condition to adapt to the biomechanics of the spine. Furthermore, the implant has an open structure. Thereby, the fusion properties are improved. The implant can be fully or partially slotted from the upper wall to the lower wall to additionally improve fusion of the implant with the surrounding. The partial bodies generated by the slot can have different widths and/or shapes.

The implant may be coated with active or non-active agents promoting in-growth of bone material, tissue or blood vessels, with pharmaceutical substances and/or with materials to facilitate sliding.

Due to the small height and optionally small width of the implant, the insertion can be carried out minimally invasive. The insertion can be performed without applying high forces, such as would be in the case in punching in the implant. Mechanisms for changing the height of the implant using a tool are not necessary. A particular field of application of the intervertebral implant is the treatment of the lumbar spine.

An instrument for inserting the intervertebral implant is configured to be connected to the intervertebral implant in the compressed condition without compressing it and is configured to be detached from the implant after placement. The instrument may have two arms or brackets that can be closed to engage the implant and can be opened to release the implant.

In a first aspect, the implant comprises an attachment projection on an outer wall of the implant, preferably on a sidewall, and the instrument may be connected to the attachment projection.

In a second aspect, the implant comprises a rotatable member provided inside the implant that can be engaged by the instrument. The instrument comprises two brackets that are configured to engage the rotatable member such that the implant and the instrument are rotatable with respect to each other.

In a third aspect, the instrument may be attached to the implant through a pivot joint provided by cylindrical projections on the arms of the instrument that are rotatably received in recesses of the implant, preferably in the upper wall and the lower wall.

In a fourth aspect, the instrument comprises a sleeve and arms in the form of wires guided through the sleeve and having each an engagement portion to engage the implant. The wires can be displaced relative to each other so that the implant can be advanced along a curved trajectory. One of the wires is used to press the implant and the other one is used to pull the implant. The wires may be made of a nickel titanium alloy.

In a fifth aspect, the instrument comprises at least one wire with a curved portion, wherein the wire is guided through the implant in a direction of insertion. The implant can be pushed along the at least one wire to be moved along a curved trajectory like in rails.

In a sixth aspect, the implant comprises keel-like teeth extending substantially in the direction of insertion. In the compressed condition, the height of the implant is such that the keel-like teeth can engage the end plates of the vertebral bodies. An instrument may be attached to one end of the implant, and the implant is guided by the engagement of the keel-like teeth with the vertebral end plates.

The instrument according to the first to sixth aspects is not limited for use in connection with the intervertebral implant according to the embodiments but can also be used with other intervertebral implants.

BRIEF DESCRIPTION OF THE DRAWINGS

Further features and advantages of the invention will become apparent from the description of some embodiments by means of the accompanying drawings. In the drawings.

DETAILED DESCRIPTION

Figure 2:
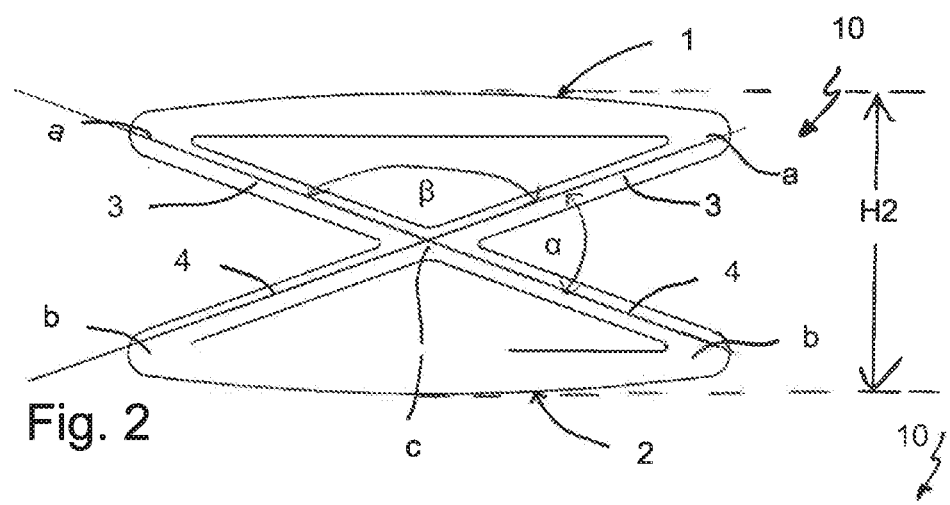
FIG. 2 shows a front view of the intervertebral implant of FIG. 1
Figure 3:
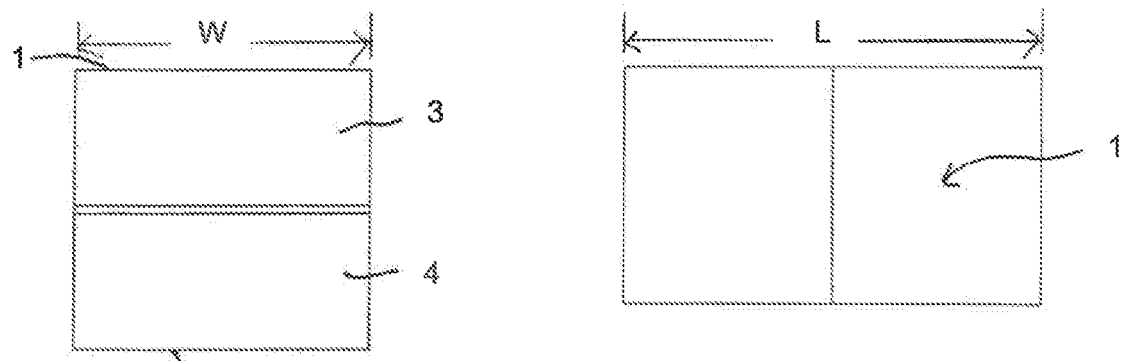
FIG. 3 shows a side view of the intervertebral implant of FIG. 1 and FIG. 2.
Figure 4:
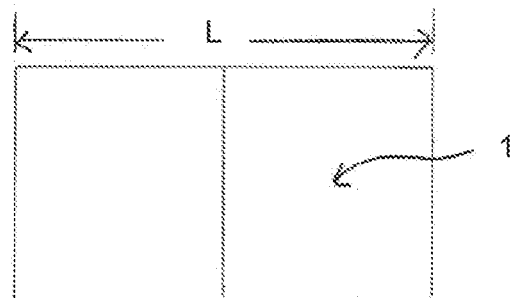
FIG. 4 shows a top view of the intervertebral implant of FIG. 1 and FIG. 2.

Turning now to FIGS. 1 to 4, an intervertebral implant 10 according to the first embodiment is a monolithic piece that comprises an upper wall 1 and a lower wall 2 that are connected through a load transmitting part. The upper wall 1 and the lower wall 2 are substantially parallel to each other. A length L of the upper wall 1 and the lower 2 that defines a lengthwise direction is such that the intervertebral implant 10 can be accommodated fully in the intervertebral space between two vertebrae. A width W of the upper wall 1 and the lower wall 2 is smaller than the length L. The upper wall 1 and the lower wall 2 are curved slightly outward or have two inclined surface portions such that a greatest height H2 of the implant 10 in the expanded condition is provided in the center of the implant in the lengthwise direction. The load transmitting part comprises two arms 3 and two legs 4, wherein the arms 3 each are connected to the upper wall 1 at connecting locations a and wherein the legs are connected to the lower wall 2 at connecting locations b. The connecting locations a and b are at the respective ends of the upper wall 1 and the lower wall 2 in the lengthwise direction. A transition between the upper wall 1 and the arms 3 as well as between the lower wall 2 and the legs 4 at the connecting locations may be rounded. In a top view, as depicted in FIG. 4, the upper wall 1 and the lower wall 2 have a rectangular contour. It shall be noted, however, that another contour may be possible, such as, for example, a trapezoidal contour, a banana-shaped contour or otherwise shaped contour.

The arms 3 are connected to each other and to the legs 4 at a connecting location c approximately at the middle between the upper wall 1 and the lower wall 2 in the height direction. Also, the connecting location c is approximately in the middle between the respective ends of the upper wall 1 and the lower wall 2 in the lengthwise direction. Hence, in a front view, as depicted in FIG. 2, the load transmitting part has substantially an X-shape. As can be seen in particular in FIG. 3, the arms 3 and the legs 4 extend across the whole width W. As further shown, the arms 3 and the legs 4 have a substantially rectangular cross-section.

An angle β between the arms 3 is approximately in the range between about 100° to about 150°. The angle α between an arm 3 and a leg 4 facing this arm 3 is 180°-β. Hence, the angle α is between about 30° and about 80°. The load transmitting part is symmetric with respect to a plane extending through the connecting location c and extending in the width direction. By means of this an optimized load transfer is provided.

Figure 1:
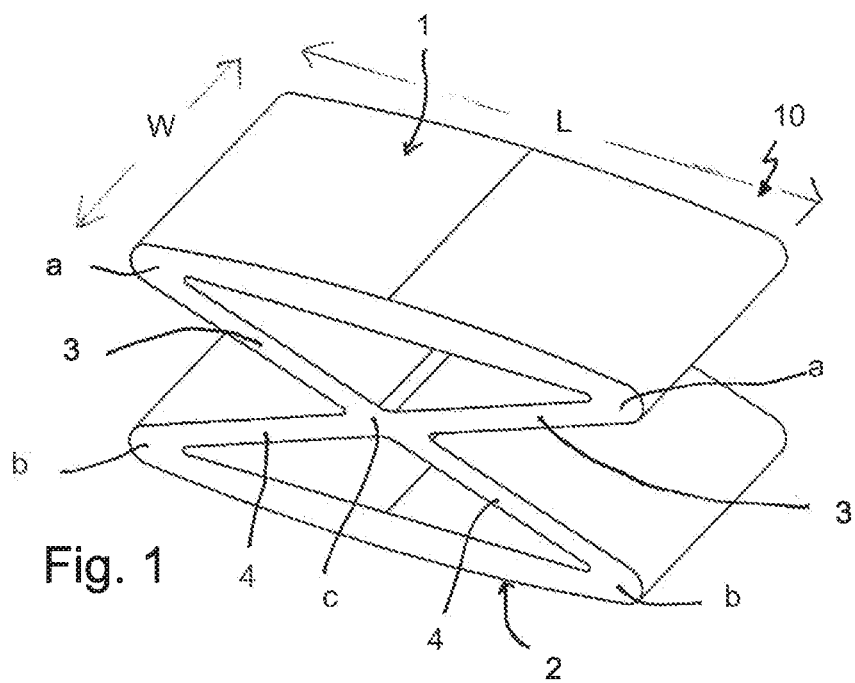
FIG. 1 shows a perspective view of a first embodiment of the intervertebral implant in the expanded condition.
Figure 5:
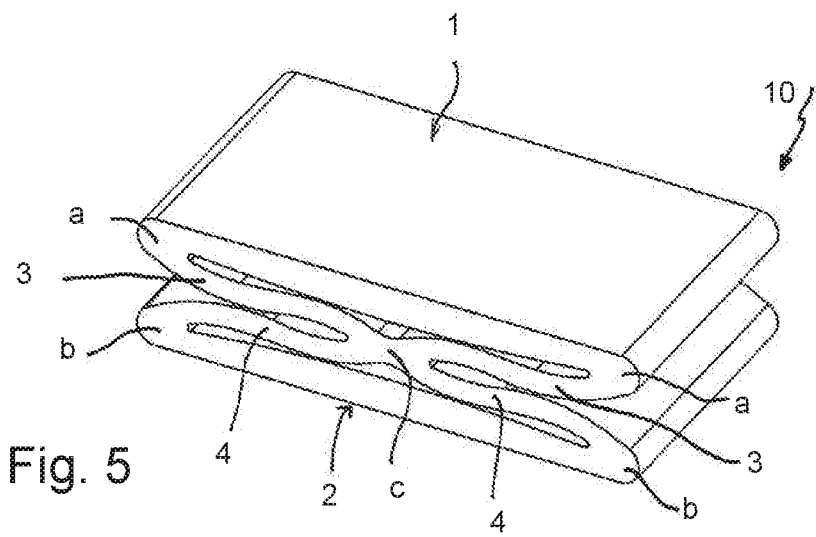
FIG. 5 shows a perspective view of the intervertebral implant of FIG. 1 to FIG. 4 in the compressed condition.
Figure 6:
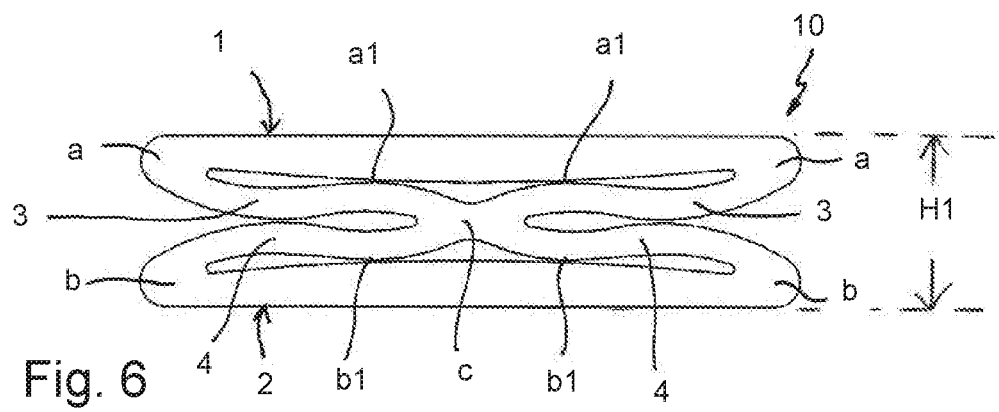
FIG. 6 shows a front view of the intervertebral implant of FIG. 5 in the compressed condition.
Figure 7:
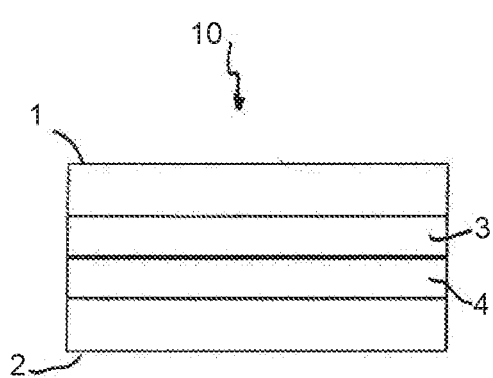
FIG. 7 shows a side view of the intervertebral implant of FIG. 5 and FIG. 6.
Figure 8:
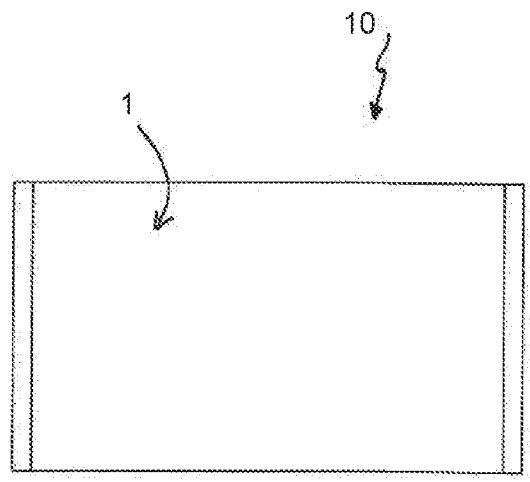
FIG. 8 shows a top view of the intervertebral implant of FIG. 5 to FIG. 7.

The implant 10 is configured to assume two end conditions, the expanded condition in which the distance H2 between the upper wall 1 and the lower wall 2 in the height direction is greatest as shown in FIGS. 1 to 3 and a compressed condition in which the distance H1 between the upper wall 1 and the lower wall 2 is smallest as depicted in FIGS. 5 to 7. In the compressed condition the arms 3 and the legs 4 are spread such that the angle β becomes larger and the angle α becomes smaller. Thereby, the arms 3 and the legs 4 assume a curved or wavy shape in the lengthwise direction as can be seen in particular in FIGS. 5 and 6. Moreover, in the compressed condition the arms 3 and the legs 4 may contact an inner surface of the upper wall 1 and the lower wall 2 at locations a1 and b1, respectively. A height difference H2 minus H1 of the implant between the expanded condition and the compressed condition may be equal to or greater than 25% of the height H2 in the expanded condition. Furthermore, in the compressed condition, the upper wall 1 and the lower wall 2 may be slightly deformed so that they provide a flat top and bottom but slightly curved inner surface facing towards the inside of the implant.

During expansion from the compressed condition to the expanded condition the intervertebral implant may assume intermediate conditions in which the distance between the upper wall 1 and the lower wall 2 is not yet the full distance H2 in the height direction.

The intervertebral implant 10 is made of a shape memory material. Such a shape memory material is preferably a shape memory alloy, such as any of nickel titanium alloys that exhibit shape memory properties, in particular Nitinol. Preferably, the material is a nickel titanium alloy with a nickel content of about 50 to 52 at. % (atomic percent) nickel, preferably about 50.2 to about 51.5 at. % nickel and most preferably 50.6 to 51.0 at. % nickel according to the standards ASTM F 2063. At a recovery level, the material has transformed into another microscopic state and can assume a memorized shape. In the case of a shape memory alloy, such as nickel titanium alloy, the recovery level may be the austenite finish temperature $A_f$ of the alloy. Preferably the austenite finish temperature $A_f$ is in the range of about 23° C. to about 32° C., and most preferably between 25° C. and 30° C. Hence, the implant 10 can expand by the application of body heat only. The implant 10 is configured to be deformable at a lower temperature to assume the compressed condition, for example at temperatures below room temperature wherein room temperature is around 23° C.±3° C. Moreover, the implant is configured to remain at a temperature of about room temperature in the compressed condition without the application of external forces. The martensite start temperature $M_s$ and the martensite finish temperature $M_f$ are tied to the austenite start temperature $A_s$ and the austenite finish temperature $A_f$ according to ASTM F 2063.

The implant 10 may be coated, for example, with polymers, active agents or metallic base materials. The polymers may be, but not limited to, ultra-high-molecular weight polyethylene (UHMWPE), high-modulus polyethylene (HMPE), high-performance polyethylene (HPPE), hydroxy apatite, polymethylmethacrylate (PMMA), polytetrafluoroethylene (PTFE), parylene, antibacterial coatings (block co-polyether ester constituted by PBT and various others such as polytetramethylene oxide (PTMO), polyethylene oxide-polypropylene oxide-polyethylene oxide (PEO-PPO-PEO), polyethylene oxide (PEO), nano-particles or nano-composites, polyether ether ketone (PEEK), CFC-PEEK, polyvinyl fluoride (PVF), poly(iso)butylene (PIB), polycarbonate urethane (PCU), polyphosphazene, polylactides (PLs) (the most important ones are here poly-L-lactides, poly-D,L-lactides, copolymers, poly(L-lactides-co-glycolides), poly(D, L-lactides-co-glycolides), poly(L-lactides-co-D, L-lactides), poly(L-lactides-co-trimethylene carbonate)), polyhydroxy butyric acid (PHBs), poly-β-hydroxyalkanoates (PHAs), polysaccharides, chitosan, levan, hyaluronic acid, heparin, dextran and cellulose. The active substances may be, but not limited to, drugs based on isoflavones or metabolites, calcium sulphate with embedded hydroxy apatite particles, hydroxy apatite and calcium sulphate mixed with gentamicin, limus compounds, preferably sirolimus (rapamycin), zotarolimus, tacrolimus, fujimycin, biolimus, everolimus. The metallic base materials may be, but not limited to, ultrapure magnesium with a magnesium content of equal to or greater than 99 at. %, silicon, calcium. In particular, magnesium of this type may enhance the ingrowth of bone material, tissue and blood vessels.

Figure 9:
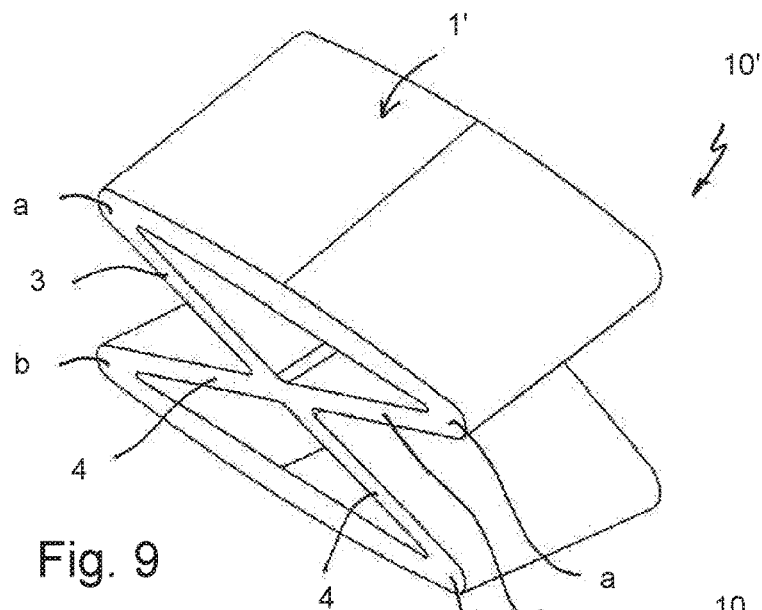
FIG. 9 shows a perspective view of an intervertebral implant according to a second embodiment in an expanded condition.
Figure 10:
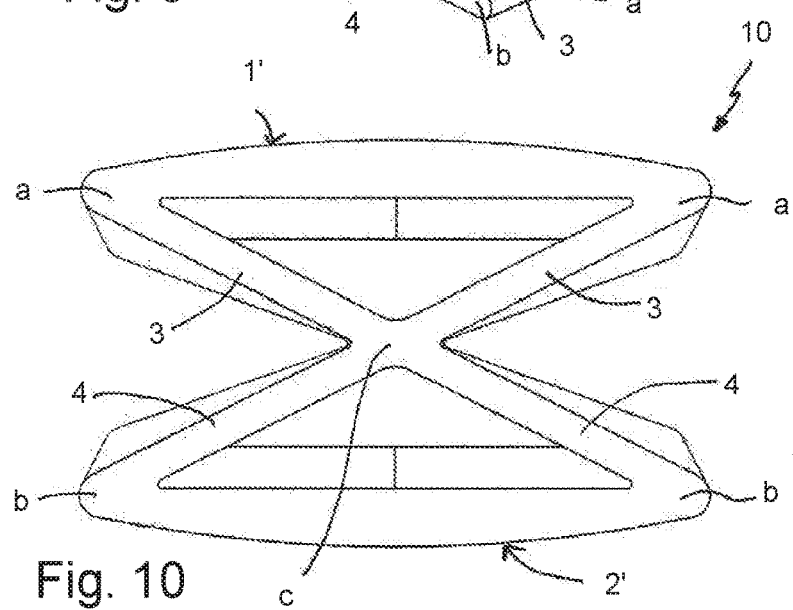
FIG. 10 shows a front view of the intervertebral implant of FIG. 9.
Figure 11:
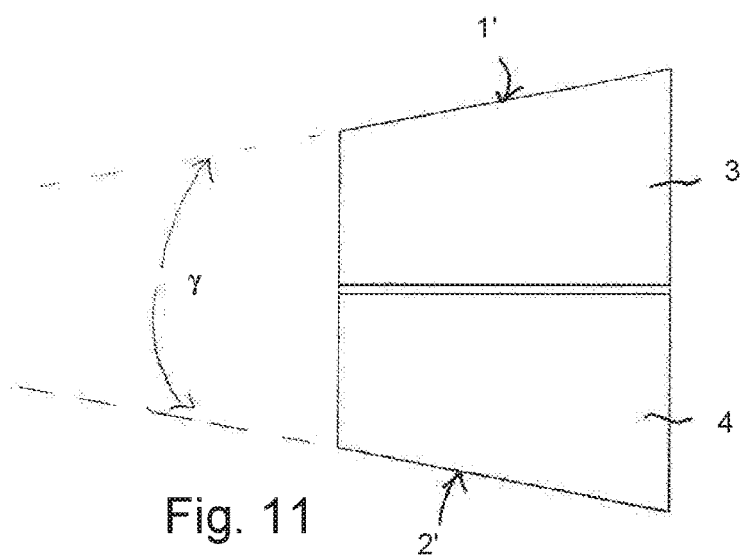
FIG. 11 shows a side view of the intervertebral implant of FIG. 9 and FIG. 10.

Referring now to FIGS. 9 to 11, a second embodiment of an intervertebral implant 10' differs from the first embodiment only in that an upper wall 1' and a lower wall 2' are inclined with respect to each other. An angle γ of inclination may be, for example, 5° or 10° or any other angle suitable for the treatment of lordotic segments of the spine. All other parts and portions are the same as for the first embodiment and the description thereof will not be repeated. The implant 10' may be used in particular for correcting lordosis.

Figure 12:
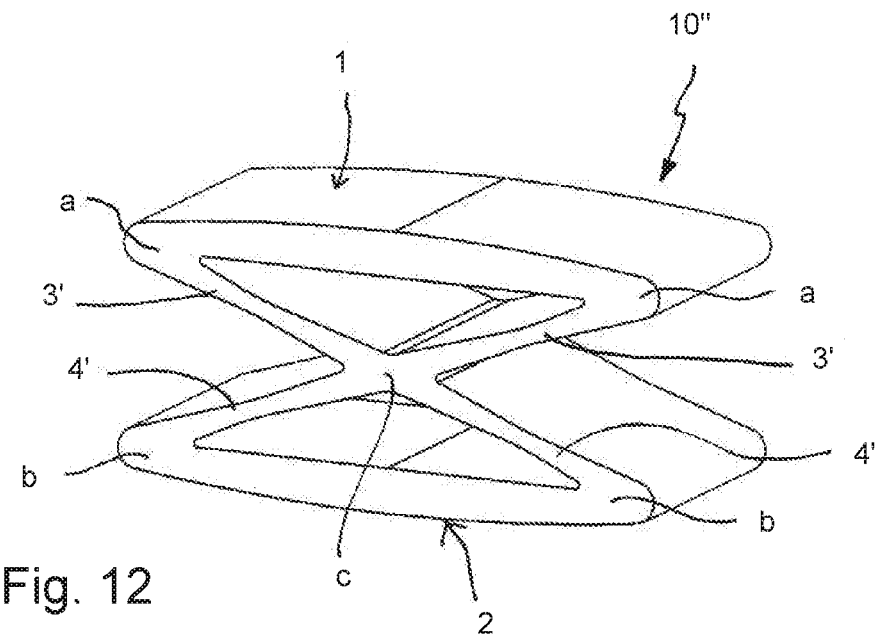
FIG. 12 shows a perspective view of an intervertebral implant according to a third embodiment in an expanded condition.
Figure 13:
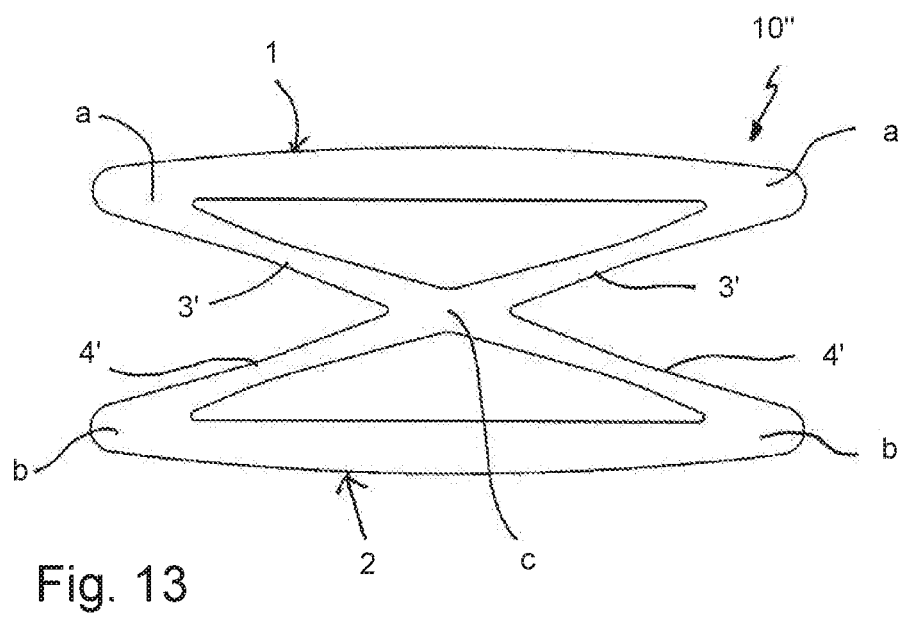
FIG. 13 shows a front view of the intervertebral implant of FIG. 12.

A third embodiment of an intervertebral implant 10" as depicted in FIGS. 12 and 13 differs from the first embodiment by the thickness of arms 3' and legs 4'. Seen in a front view, the thickness of the arms 3' and of the legs 4' is smallest between the connecting locations a and c, or b and c, respectively. The enhanced thickness towards the connecting locations a and b provides for a high strength of the implant in the expanded condition while permitting deformation of the implant at low temperatures to bring it in the compressed condition. The thickness near the connecting locations a and b may be about two times the thickness of the arms 3' and the legs 4' in the middle between the connecting location a and the connecting locations a and b, respectively. It shall be noted that the implant according to the third embodiment can also have inclined upper and lower walls.

Figure 14:
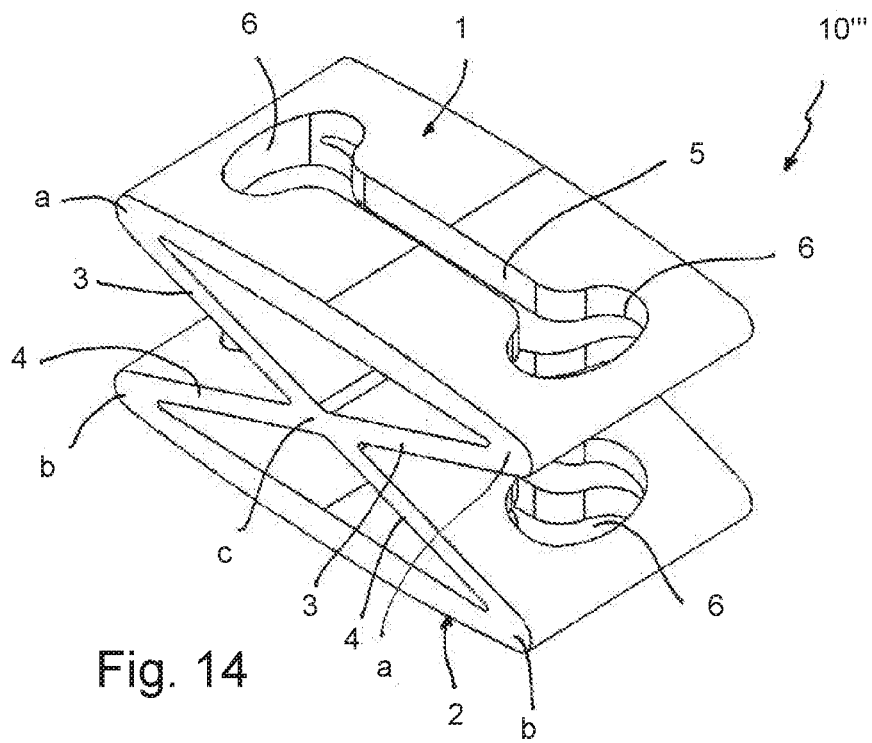
FIG. 14 shows a perspective view of an intervertebral implant according to a fourth embodiment in an expanded condition.
Figure 15:
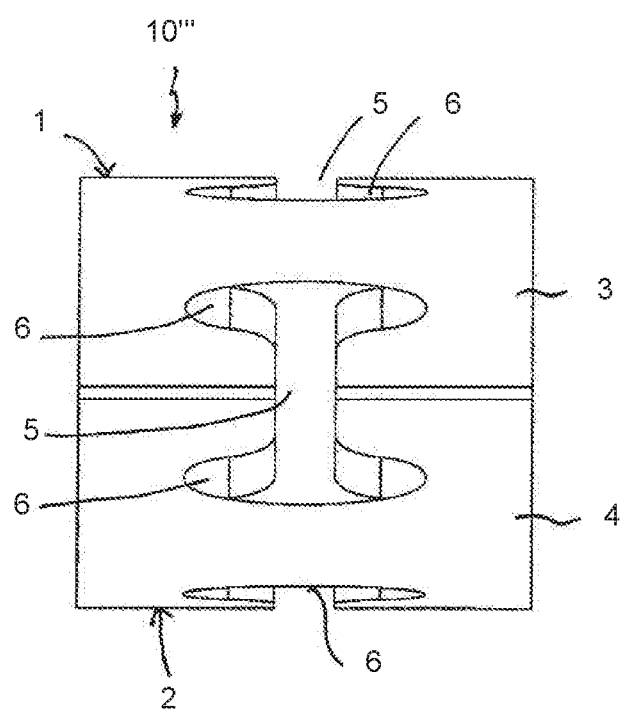
FIG. 15 shows a side view of the intervertebral implant of FIG. 14.

A fourth embodiment of the implant is illustrated in FIGS. 14 and 15. An implant 10''' differs from the implant according to the first embodiment by the provision of an elongate slot 5 that extends in the lengthwise direction through the upper wall 1 and the lower wall 2 as well as through the arms 3 and the legs 4. On both of its ends the slot 5 opens into recesses 6 that may have a circular shape. The recesses 6 also extend from the upper wall 1 to the lower wall 2 through the arms 3 and the legs 4. The purpose of the slot 5 is to form an open structure for facilitating in-growth of surrounding material such as bone material, tissue, and blood vessels, etc. The recesses 6 may have any other shape or may even be omitted. However, the recesses 6 and the slot 5 may allow to compress the implant also in the widthwise direction.

Figure 16:
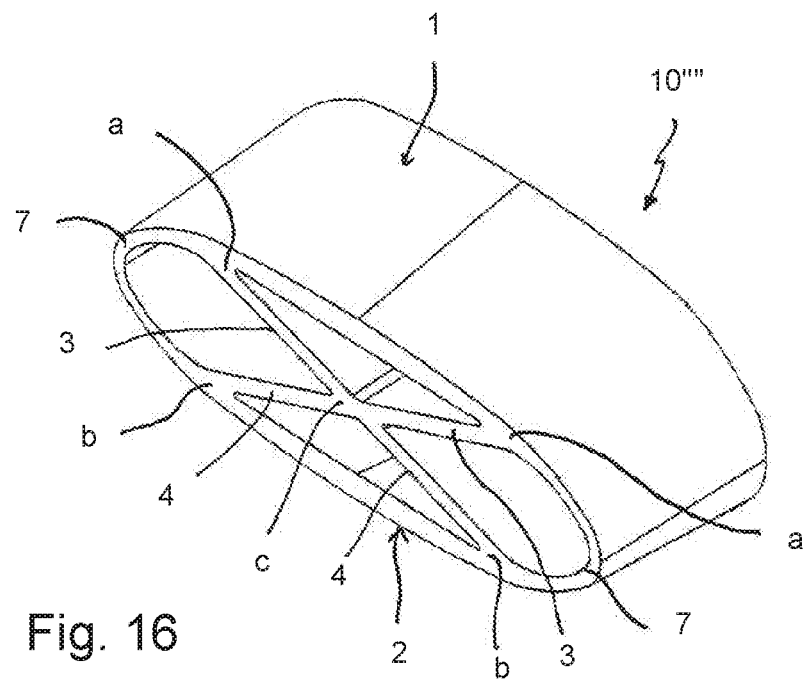
FIG. 16 shows a perspective view of an intervertebral implant according to a fifth embodiment in an expanded condition.
Figure 17:
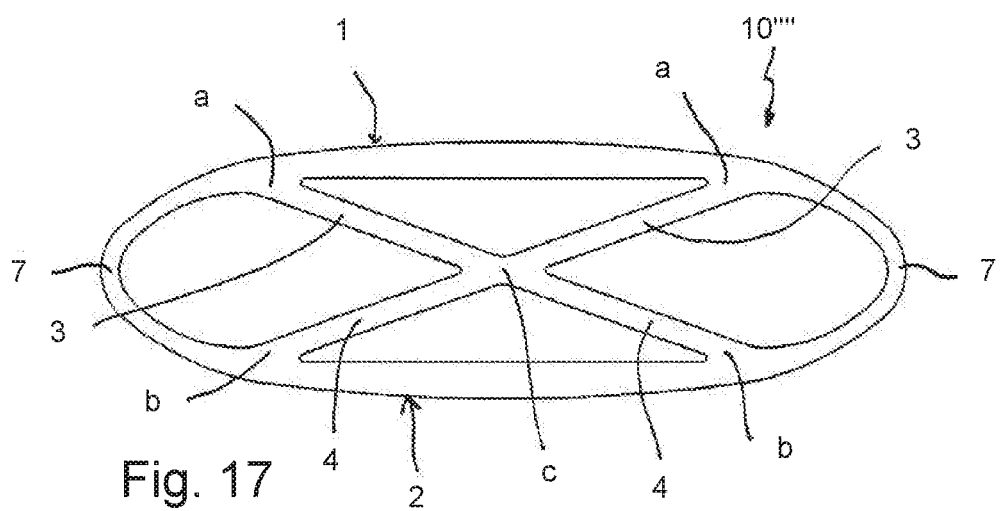
FIG. 17 shows a front view of the intervertebral implant of FIG. 16.

An implant 10"" according to a fifth embodiment as depicted in FIGS. 16 and 17 additionally comprises sidewalls 7 that connect the upper wall 1 and the lower wall 2 at both ends such that the upper wall 1 and the lower wall 2 and the sidewalls 7 form a closed loop. The sidewalls 7 may be convexly curved outward, and the height of the implant decreases towards the center of the sidewalls 7 in the lengthwise direction to facilitate insertion of the implant. By the sidewalls 7, the torsional stiffness of the implant may be enhanced. Furthermore, the sidewalls 7 may serve for attaching an instrument thereto as described more in detail below.

Figure 18:
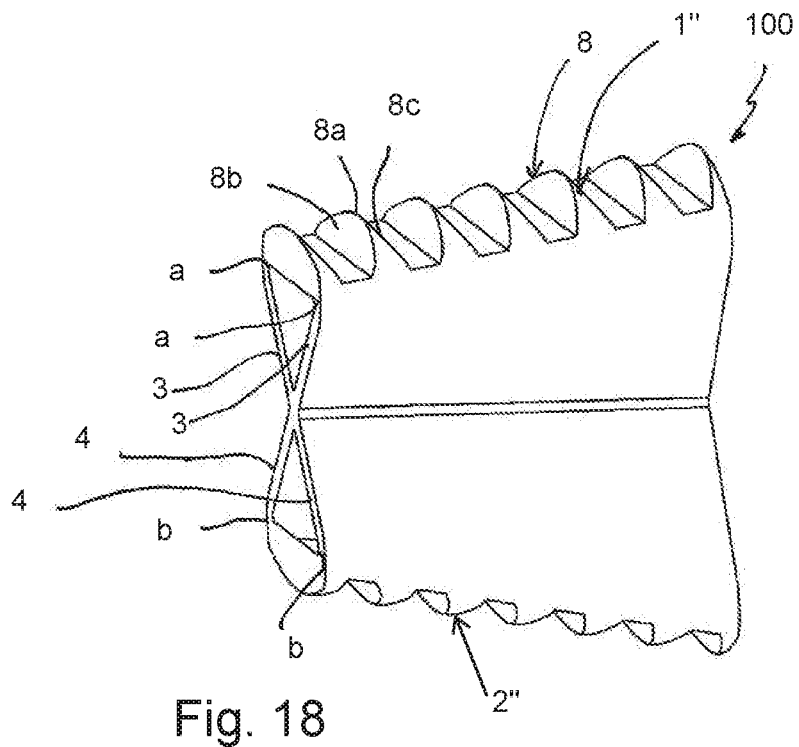
FIG. 18 shows a perspective view of an intervertebral implant according to a sixth embodiment in an expanded condition.
Figure 19:
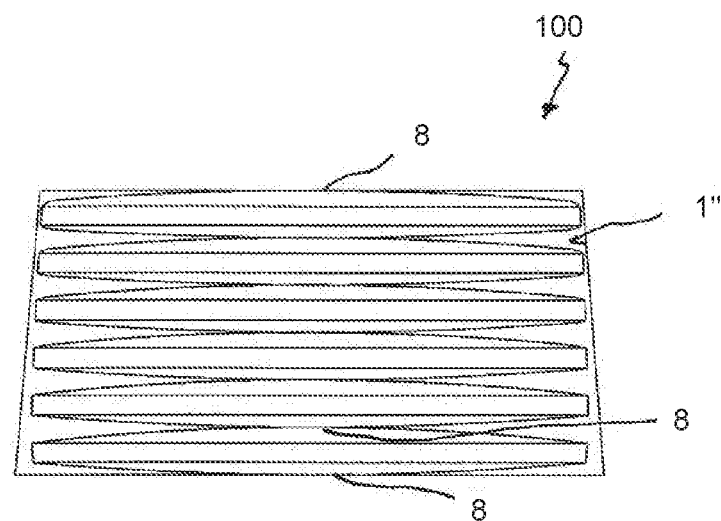
FIG. 19 shows a top view of the intervertebral implant of FIG. 18.

Turning now to FIGS. 18 and 19, a sixth embodiment of an implant 100 comprises an upper wall 1" and a lower wall 2" with a plurality of bone engagement portions or teeth 8 for engaging the vertebral end plates. Furthermore, the upper wall 1" and the lower wall 2" include an angle with each other. All other parts and portions are the same as in the first embodiment and the description thereof will not be repeated. The teeth 8 are arranged in rows along the width direction and extend continuously in the lengthwise direction. As illustrated in particular in FIG. 18, the teeth 8 have a keel-like shape with a sharp crest 8a. The flank 8b that faces towards the front side of the implant may have a different steepness, for example may be steeper, than the flank 8c that faces towards the backside of the implant. However, depending on the application, the keel-like teeth 8 may have symmetric flanks also. As can be seen in FIG. 18, one row of teeth may be provided at the outermost position of the upper wall 1" and the lower wall 2" in the widthwise direction. The height of the teeth may decrease towards the outer ends of the row to facilitate insertion. In a process of inserting the implant between the vertebral bodies, the teeth 8 with the keel-like shape do not form an obstacle if there is contact with the vertebral end plates during insertion because the crests are continuous in the lengthwise direction. After placement of the implant, the teeth 8 may serve as fixation against displacement in a lateral direction perpendicular to an insertion direction.

Figure 20:
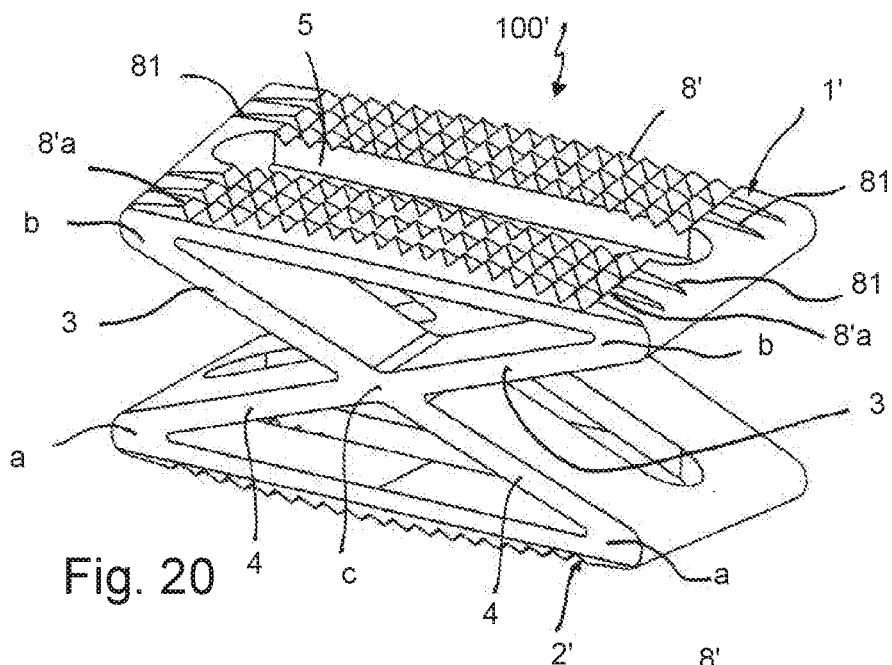
FIG. 20 shows a perspective view of an intervertebral implant according to seventh embodiment in an expanded condition.
Figure 21:
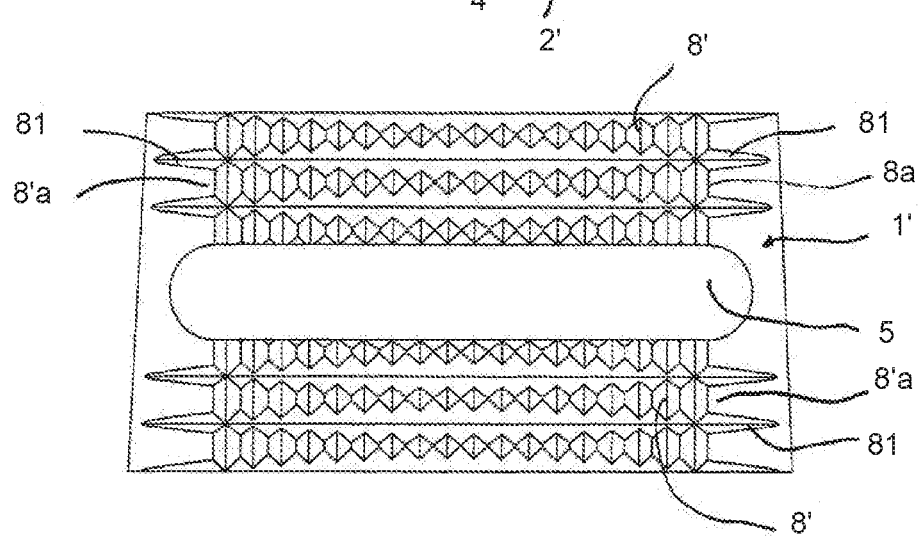
FIG. 21 shows a top view of the intervertebral implant of FIG. 20.
Figure 22:
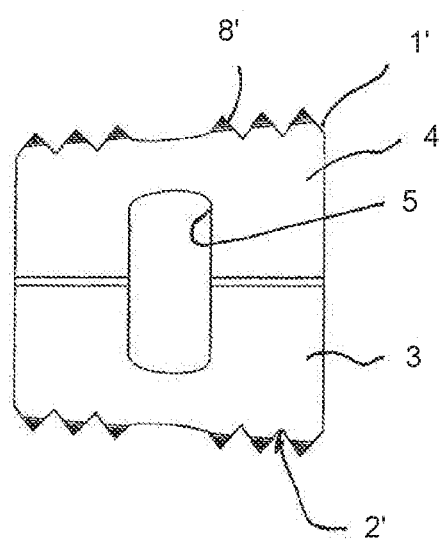
FIG. 22 shows a side view of the intervertebral implant of FIG. 20 and FIG. 21.

Another example for an implant comprising teeth on the upper wall and the lower wall is shown in FIGS. 20 to 22. An implant 100' according to a seventh embodiment comprises rows of pyramid-shaped teeth 8' on the upper wall 1' and the lower wall 2'. Also in this embodiment, the upper wall 1' and the lower wall 2' include an angle with respect to each other. The height of the teeth 8' measured from the surface of the upper wall 1' and the lower wall 2', respectively, decreases towards the center of the upper wall 1' and the lower wall 2' in the lengthwise direction. This guarantees that in the expanded condition most or all of the teeth 8' engage the surface of the vertebral end plates. Additionally, the width of the teeth 8' in the widthwise direction may decrease towards the ends of the upper wall 1' and the lower wall 2'. The rows of teeth 8' are provided only in an area between the connecting locations a and b. At the ends of the upper wall 1' and the lower wall 2', elongate teeth 8'a are provided that have a decreasing height towards the outermost ends for facilitating insertion. The elongate teeth 8'a are separated by V-shaped notches 81 narrowing towards the outer ends of the upper wall 1' and the lower wall 2'. The implant 100' may also have an elongate through-slot 5.

Figure 23:
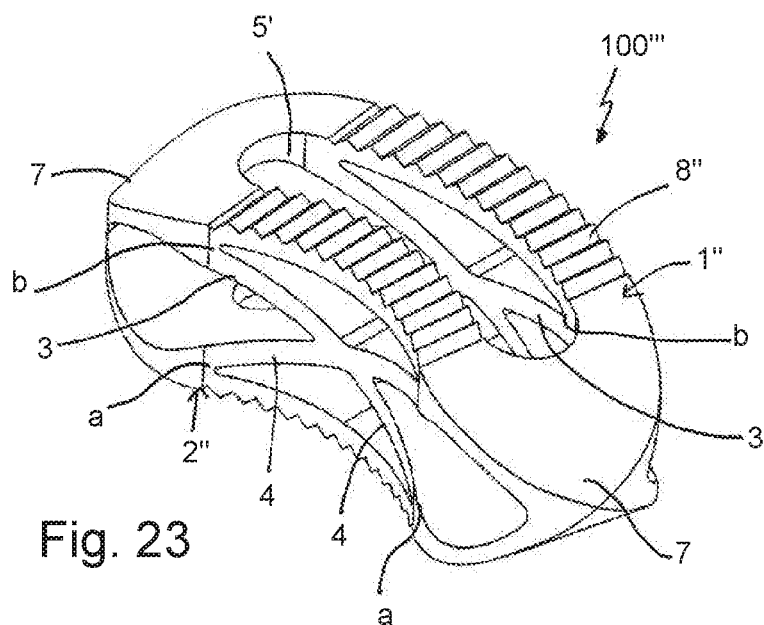
FIG. 23 shows a perspective view of an intervertebral implant according to an eighth embodiment in an expanded condition.
Figure 24:
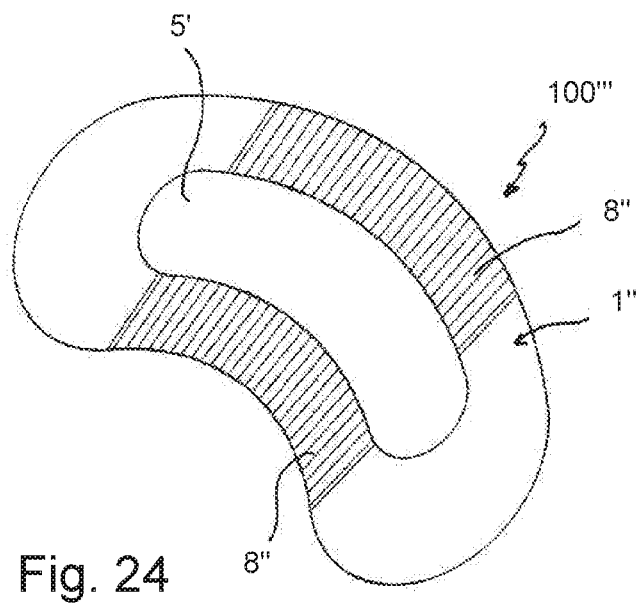
FIG. 24 shows a top view of the intervertebral implant of FIG. 23.

Turning now to FIGS. 23 to 24, an eighth embodiment of the intervertebral implant is shown. An intervertebral implant 100''' has a convex curvature seen from the front side. When seen in a top view, the contour of the intervertebral implant 100''' is banana- or kidney-shaped. Such an implant may be suitable for the TLIF (transforaminal interbody fusion) procedure. The upper wall 1" and the lower wall 2" comprise rows of teeth 8" wherein the crests extend in the widthwise direction. A through-slot 5' is provided that extends through the implant from the upper wall 1" to the lower wall 2" and has a curvature corresponding to the curvature of the upper wall 1" and the lower wall 2". As can be seen in the figures, the crests of the teeth extend continuously from the edges of the upper wall 1" and the lower wall 2" in the widthwise direction. Furthermore, the teeth 8" are provided only in an area between the connecting locations a and b, respectively. Sidewalls 7 are provided that connect the upper wall 1" and the lower wall 2". The sidewalls 7 may narrow in the widthwise direction towards the outermost ends of the implant to facilitate insertion.

Figures 25, 26:
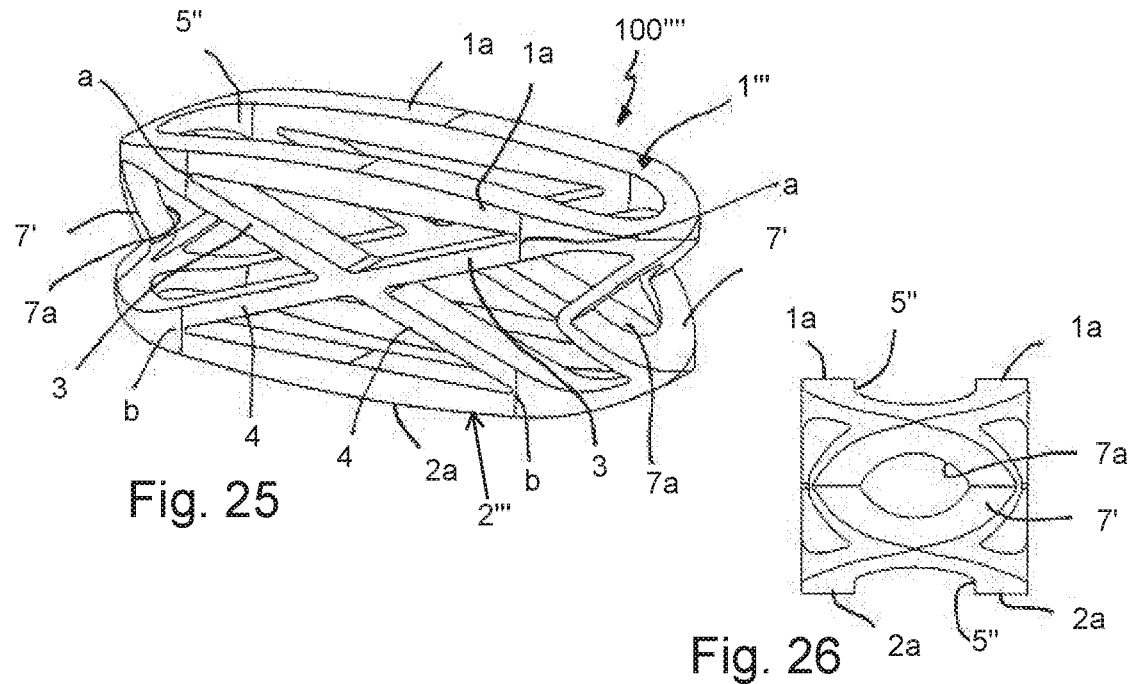
FIG. 25 shows a perspective view of an intervertebral implant according to a ninth embodiment in an expanded condition.
FIG. 26 shows a side view of the intervertebral implant of FIG. 25.

Next, a ninth embodiment of the implant is described referring to FIGS. 25 and 26. An implant 100'''' is formed without a curved contour, thus being suitable for an XLIF (extreme lateral interbody fusion) procedure. The implant 100'''' has a through-slot 5" that has such a width that an upper wall 1''' and a lower wall 2''' are formed by only strut-like portions 1a, 2a, as best seen in FIG. 26. Sidewalls 7' are provided that have a V-contour with the tip of the V-contour directed towards the center of the implant 100''''. An opening 7a is provided at the center of each sidewall 7' that may serve for attaching an instrument and contributes to the open structure of the implant 100''''.

Figures 27, 28:
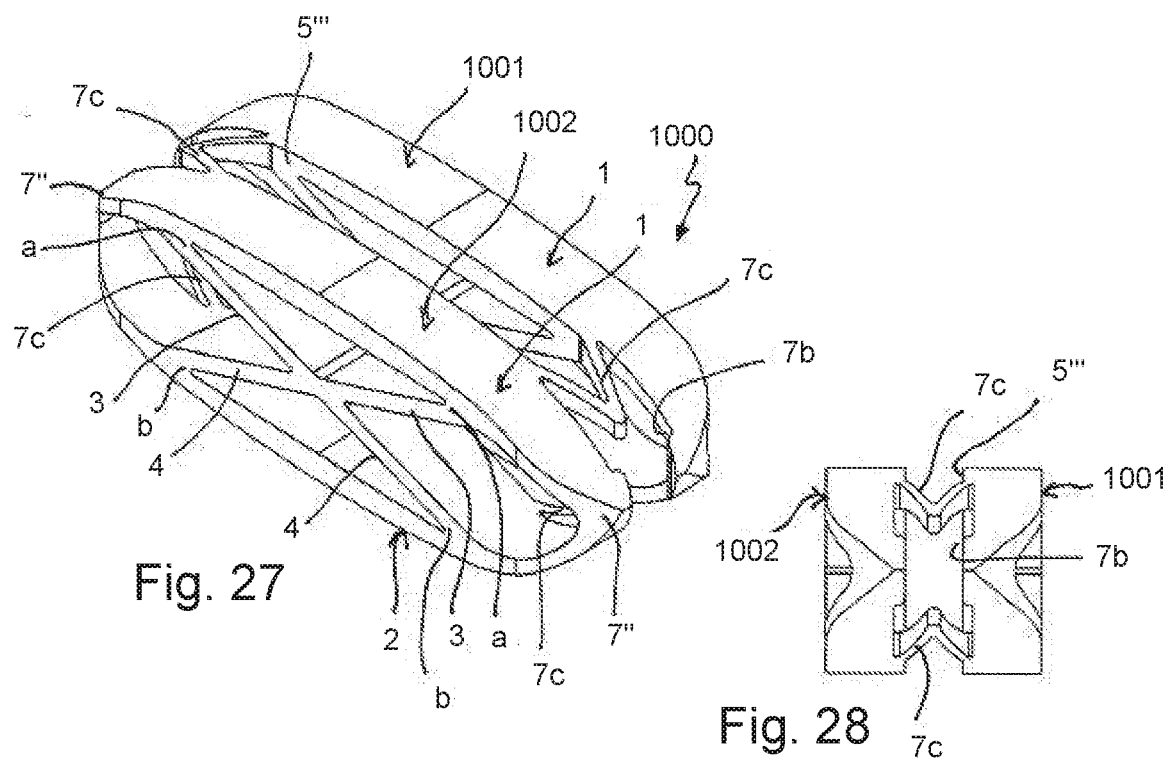
FIG. 27 shows a perspective view of an intervertebral implant according to a tenth embodiment in an expanded condition.
FIG. 28 shows a side view of the intervertebral implant of FIG. 27.

Next, a tenth embodiment of the implant is described with respect to FIGS. 27 to 28, wherein the implant has a straight contour. A through-slot 5''' extends completely through an implant 1000 from the upper wall 1 to the lower wall 2. A contour of the outer ends of the through slot 5''' in the lengthwise direction is V-shaped with a tip of the V-shape pointing towards the outer ends of the implant in the lengthwise direction. The upper wall 1 and the lower wall 2 are connected by sidewalls 7'' wherein the sidewalls 7'' comprise a slot 7b of approximately the same width as the slot 5'''. The ends of the slot 7b have a V-shaped contour with the tip of the V-shape pointing towards the outer end of the implant in the lengthwise direction. Hence, by the slots 7b and the slot 5''', the implant 1000 is divided in two bodies 1001, 1002 that are connected to each other via V-shaped struts 7c. At approximately the center of the sidewall 7'' in the height direction the slot 7b may be narrower than in the remaining portion towards the V-shaped strut 7c. By this design, the implant 1000 is composed of basically two implant bodies that are arranged in parallel and connected through a structure that allows compression of the implant 1000 also in the width direction. Hence, when the compressed implant 1000 is inserted, it may expand not only in the height direction but also in the width direction.

Turning now to FIGS. 29A to 29D, a procedure of insertion of the implant between two adjacent vertebrae is illustrated. Although an implant 10 of the first embodiment is shown, the procedure is the same or similar for all other implants according to the embodiments described above or for implants having a combination of the features of the embodiments described above. The implant 10 is brought into the compressed condition. This is effected by cooling the implant, for example by treatment with 0.9% NaCl solution such that it can be deformed. A tool may be used for the deformation, for example, a crimping device (not shown). The temperature at which the deformation can be effected is preferably below room temperature.

Figure 29A:
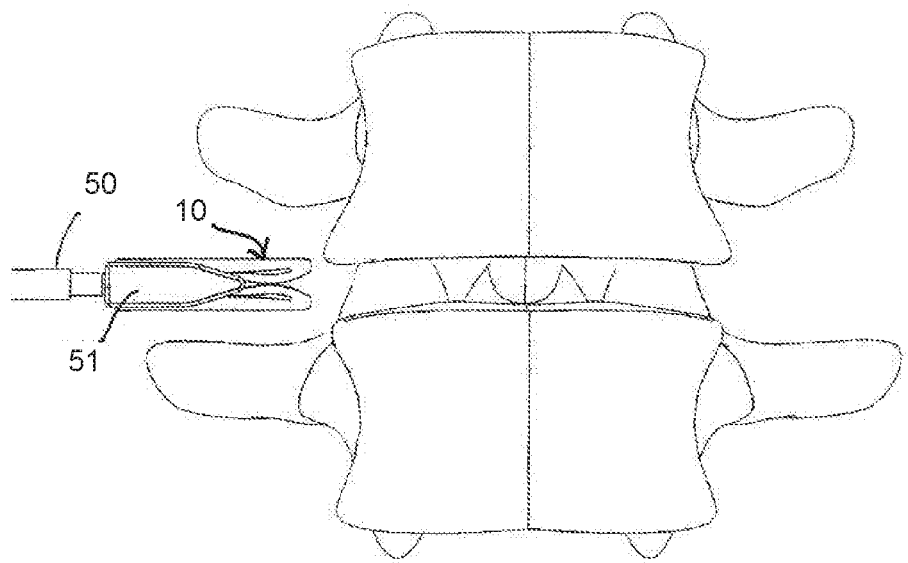
FIG. 29A to FIG. 29D show steps of inserting the intervertebral implant according to one of the previous embodiments and expansion of the implant.
Figure 29B:
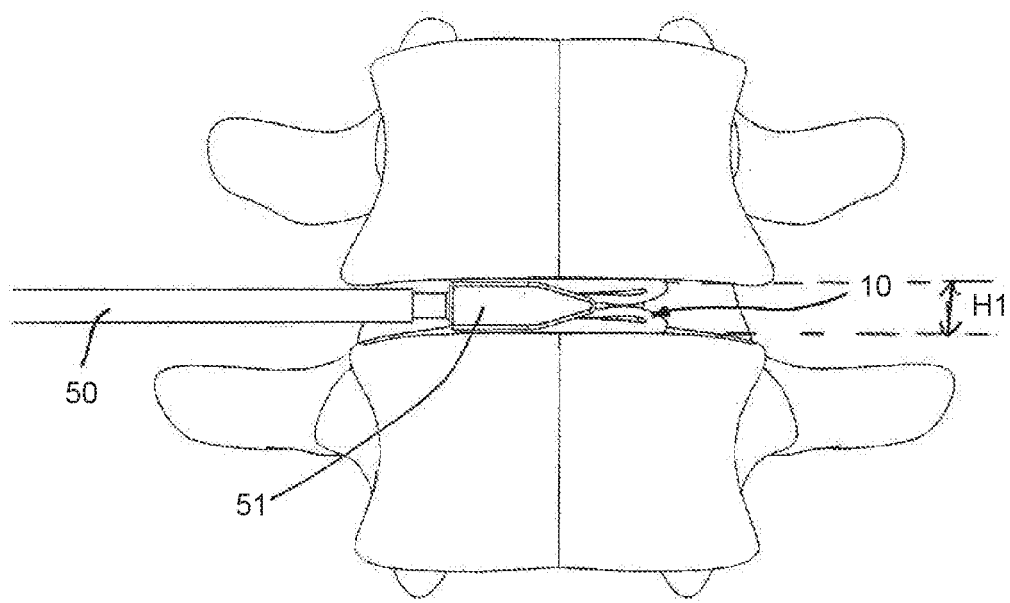
Figure 29C:
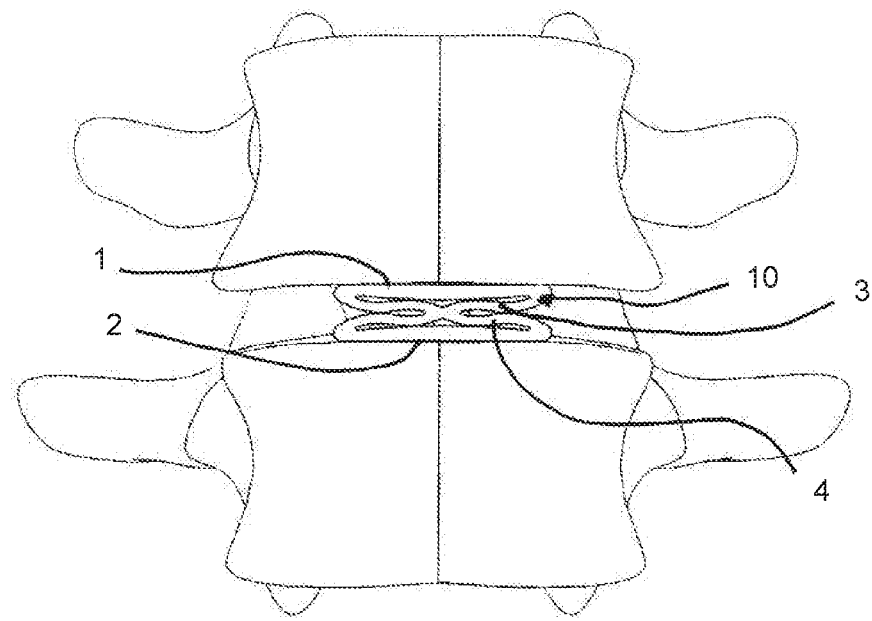

The implant can be compressed so that it has the height H1. Optionally, if the design of the implant allows, the implant can also be compressed in the width direction. After compressing the implant, the implant is attached to an instrument 50. The instrument 50 may have two brackets 51 that can assume a closed position to hold the implant and that can assume an open position to release the implant. The brackets 51, one of which is depicted in the figures, may hold the implant at the connection location c of the arms 3 and the legs 4 or at any other position. The instrument 50 is configured to hold the implant without exerting external forces that maintain the implant in the compressed condition. Rather, the implant remains in the compressed condition by itself, because the temperature to which it is exposed is well below the recovery level. Then, as depicted in FIGS. 29A and 29B, the intervertebral implant 10 is introduced into the intervertebral space using, for example, a lateral approach. The rounded transition portions between the upper wall 1 and the lower wall 2 serve for smoothly inserting the implant 10. If the implant has teeth on the upper wall and the lower wall, the teeth may be in the compressed condition below the portion with the greatest height of the implant so that during insertion the vertebral end plates are protected from being injured. After placement of the implant 10, the instrument 50 is actuated to release the implant so that the implant is between the vertebrae in the compressed condition as depicted in FIG. 29C.

Figure 29D:
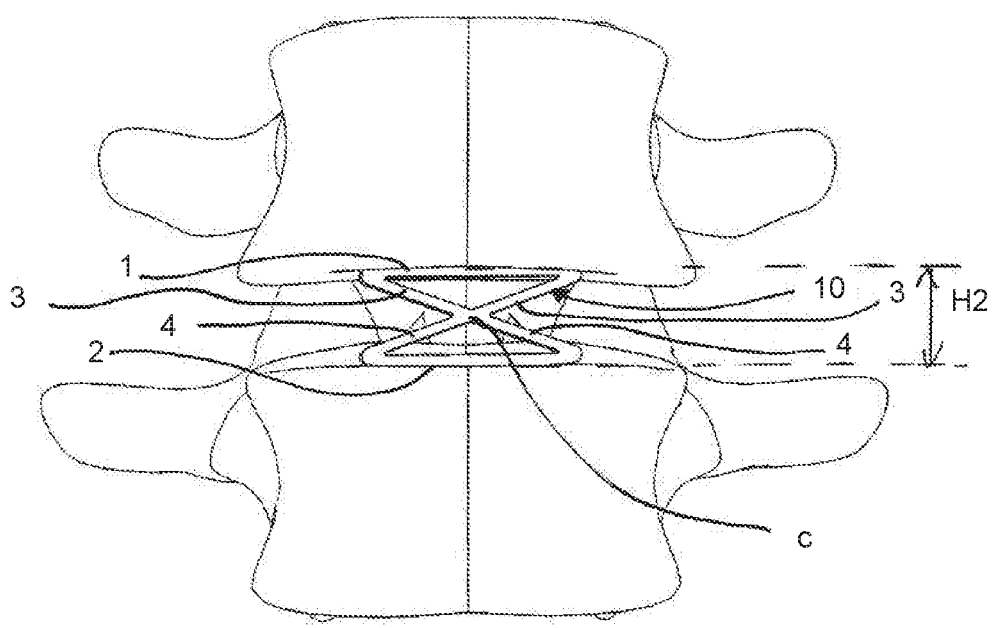

Then, by the action of the body heat the implant 10 begins to expand, thereby enlarging the intervertebral space until it has achieved the expanded condition with the greatest height H2, as shown in FIG. 29D. In the expanded condition, the arms 3 and the legs 4 bear the load that acts onto the upper wall 1 and transmit it to the lower wall 2. Due to the superelastic material, the implant is less rigid as with a conventional material, such as titanium. If the implant comprises the bone engagement portion such as the teeth, the teeth engage the vertebral end plate to prevent movement of the intervertebral implant 10. If the implant has been compressed also in the width direction, the expansion under the influence of the body heat also takes place in the width direction, thereby permitting a load transfer of a greater width which renders the implant 10 more stable. If the implant has engagement portions in the form of the keel-like teeth that extend substantially into the insertion direction, the keel-like teeth may provide guiding structure for guiding the insertion of the implant in a lateral approach.

Figure 30:
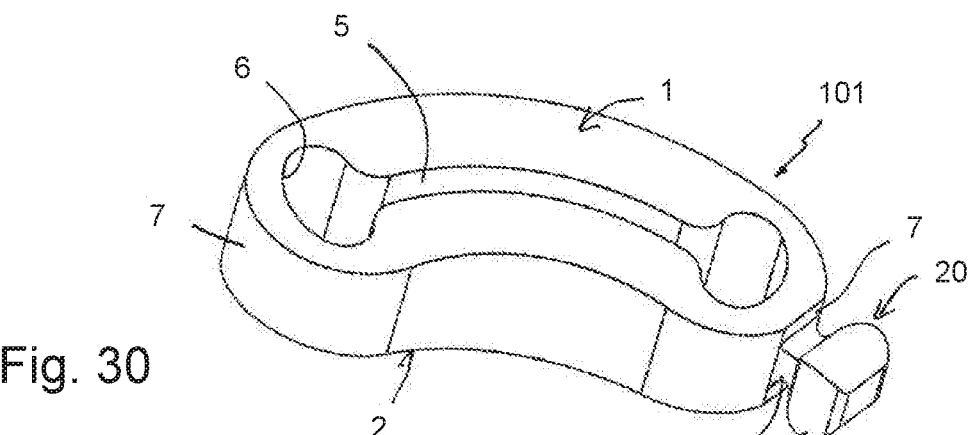
FIG. 30 shows schematically a perspective view of an intervertebral implant with an attachment projection on an outer wall for attaching an instrument.
Figure 31:
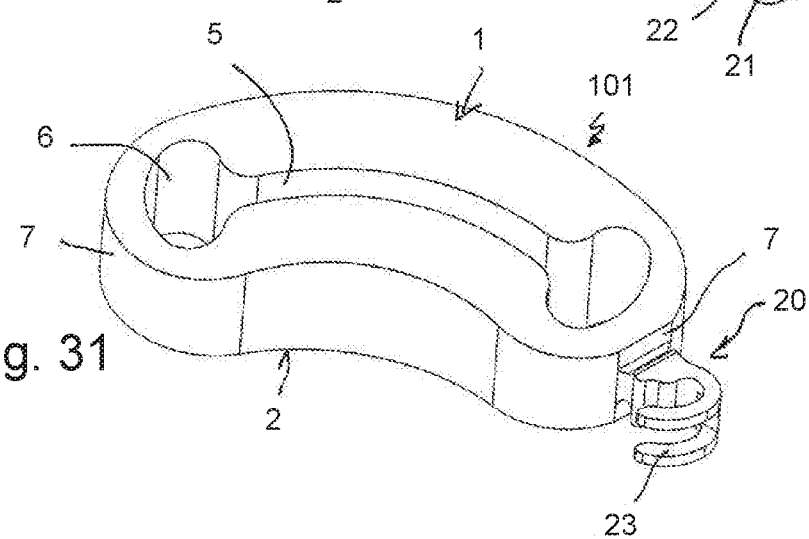
FIG. 31 shows schematically a perspective view of an intervertebral implant with a modified attachment projection on an outer wall for attaching an instrument.
Figure 32:
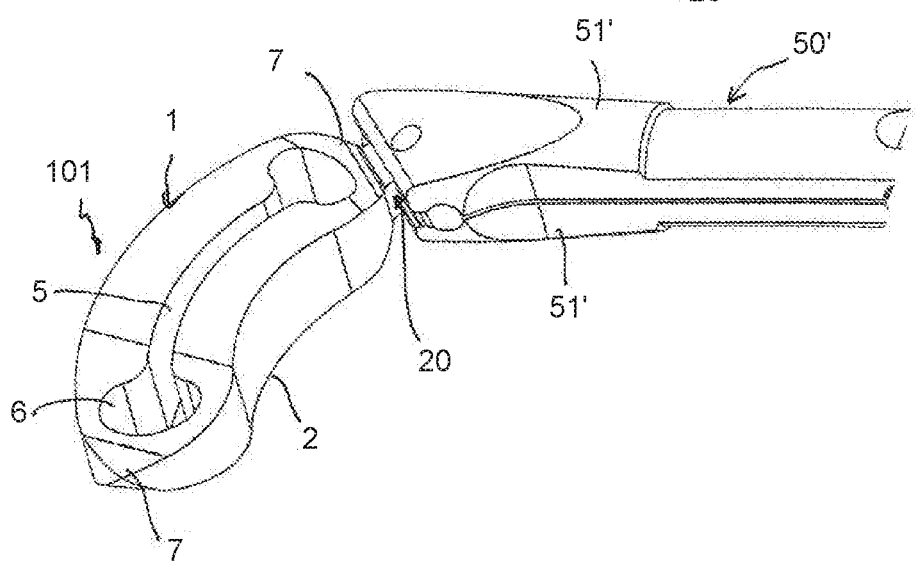
FIG. 32 shows schematically a perspective view of an intervertebral implant with an attachment projection according to FIG. 30 or FIG. 31 and an instrument attached thereto.

In the following, aspects of attaching an instrument to the implant are shown. FIGS. 30 to 32 show schematically in a perspective view a first aspect of attaching an instrument to the implant, wherein the instrument is attached at the outside, more specifically at one outer end of the implant. An implant 101 shown in FIGS. 30 to 32 is only a schematic representation of an implant wherein the arms and the legs of load transmitting part of the embodiments of the implants described before are omitted. The implant 101 has an upper wall 1 and a lower wall 2 and connecting sidewalls 7. At one of the sidewalls 7 an outer connection structure 20 is provided. In FIG. 30 the connection structure 20 has the shape of a knob 21 that is connected to the implant through a neck portion 22 with a smaller outer diameter or width than the knob 21. In the example shown in FIG. 31, the outer connection structure 20 is a double hook 23. The double hook 23 defines an axis of rotation that is perpendicular to the upper wall and the lower wall and hence, if the corresponding instrument has an engagement axis, the implant 101 can rotate with respect to the instrument to some extent.

FIG. 32 schematically shows the engagement of the outer connection portion by an instrument 50' having two brackets 51' that are in a closed position to hold the connection or engagement portion 20. The brackets 51' may be opened to release the implant 101.

Figure 33:
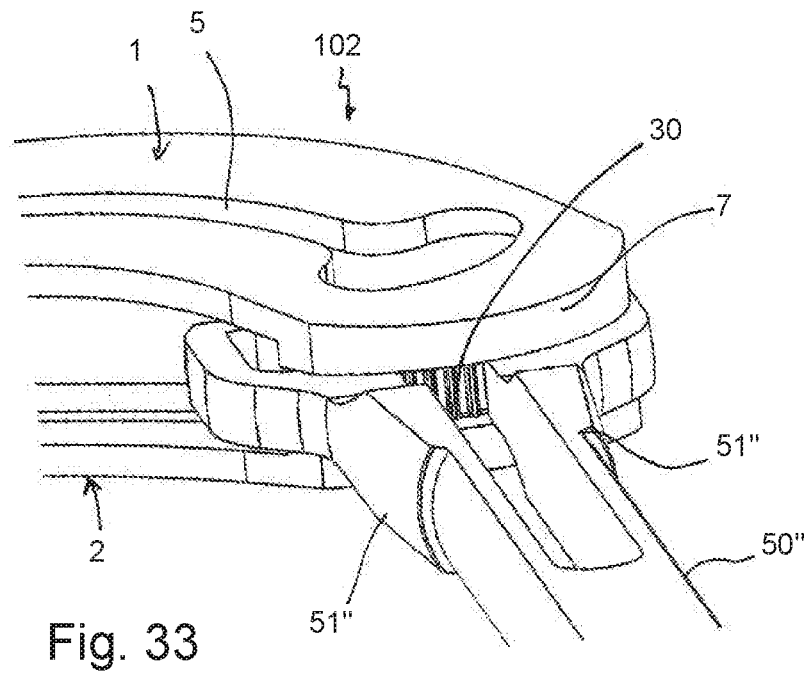
FIG. 33 shows schematically a perspective view of an intervertebral implant with a rotatable member inside the implant and an instrument attached to the rotatable member.
Figure 34:
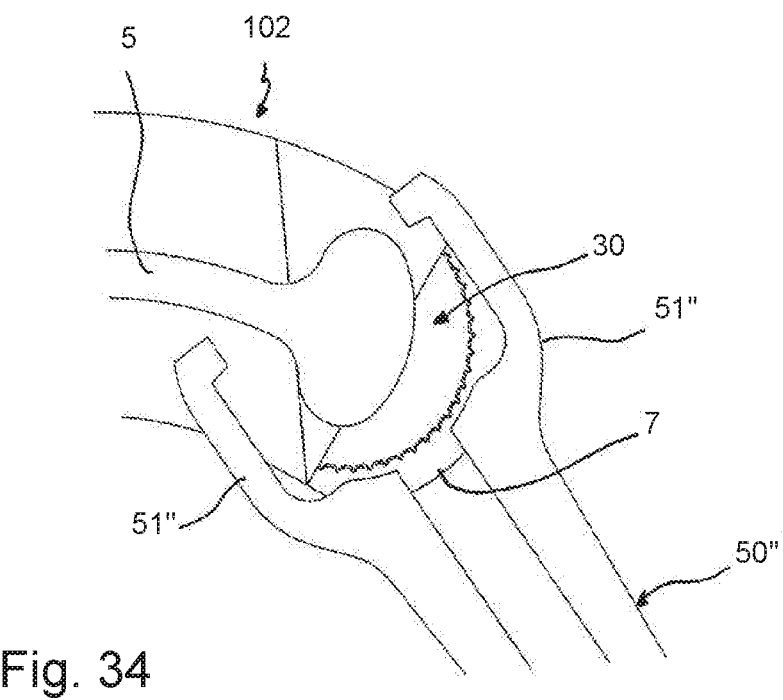
FIG. 34 shows schematically the intervertebral implant and the rotatable member of FIG. 33 and an instrument attached thereto.

Referring to FIGS. 33 and 34, a second aspect of attaching an instrument to the implant involves the provision of a rotatable member that can be engaged by the instrument to permit a rotation of the implant relative to the instrument. This is useful if the implant is inserted along a curved trajectory into the intervertebral space. As depicted in FIG. 33, an implant 102 comprises a rotatable sleeve 30 that is accommodated in the implant 102 at a location near one of the sidewalls 7. An axis of rotation is substantially perpendicular to the upper wall 1 and the lower wall 2 if the upper wall 1 and the lower wall 2 are substantially parallel. In the case of a lordosis and inclined upper and lower walls, the axis of rotation intersects the upper wall and lower wall at an angle that is defined by the angle of inclination of the upper wall and the lower wall. The rotatable member 30 may have an outer gripping structure, such as longitudinal ripples or flutes that can be gripped by the instrument. The instrument 50" comprises two brackets 51" that are configured to engage the rotatable member 30 and to firmly hold the rotatable member 30. By this design, the body of the implant 102 is rotatable with respect to the instrument 50" so that the implant 102 can be inserted along a curved trajectory.

Figure 35:
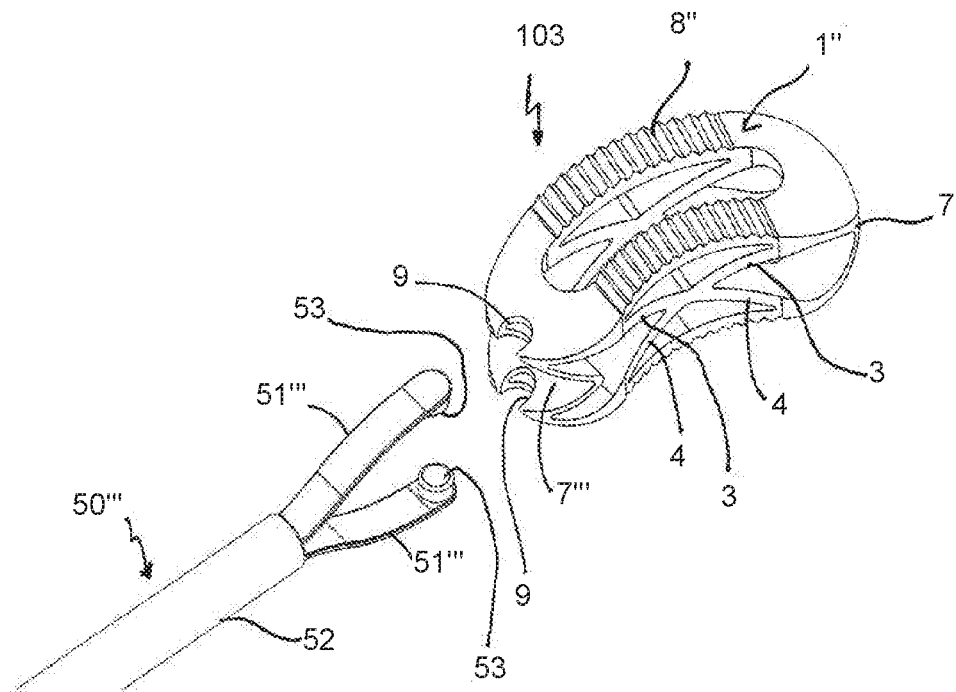
FIG. 35 shows a perspective view of an intervertebral implant and an instrument connectable thereto in the manner of a pivot joint.
Figure 36:
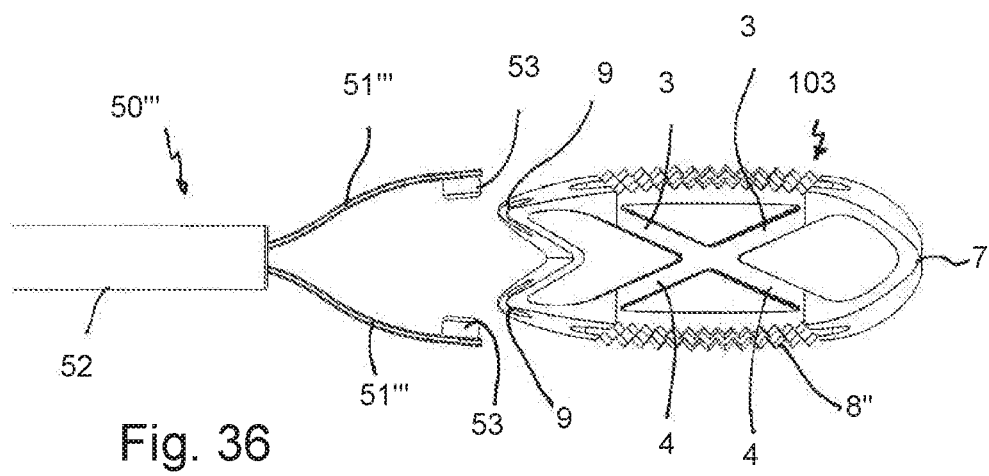
FIG. 36 shows a front view of the intervertebral implant and a side view of the instrument of FIG. 35.
Figure 37:
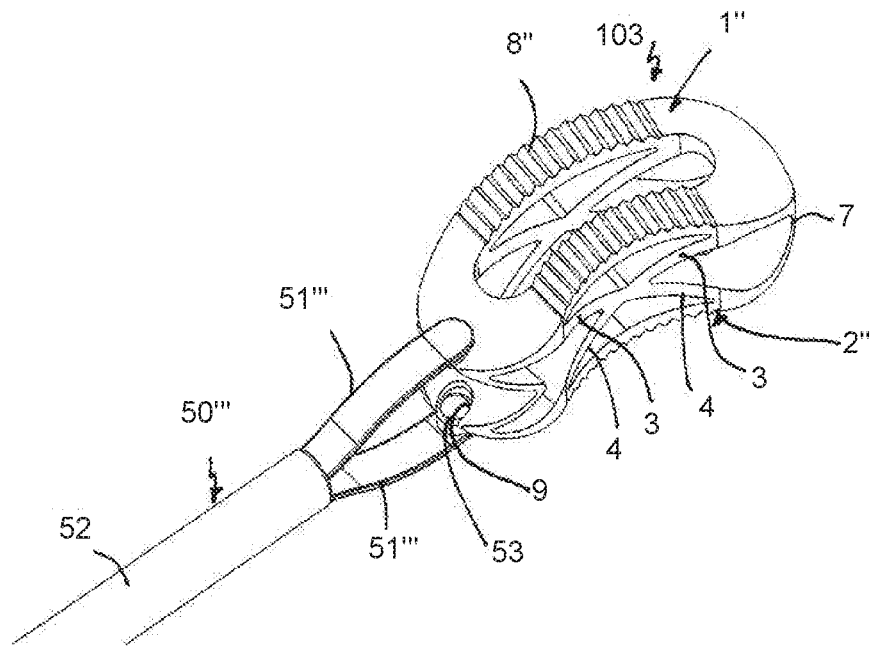
FIG. 37 shows a perspective view of the intervertebral implant of FIGS. 35 and 36 engaged by the instrument.
Figure 38:
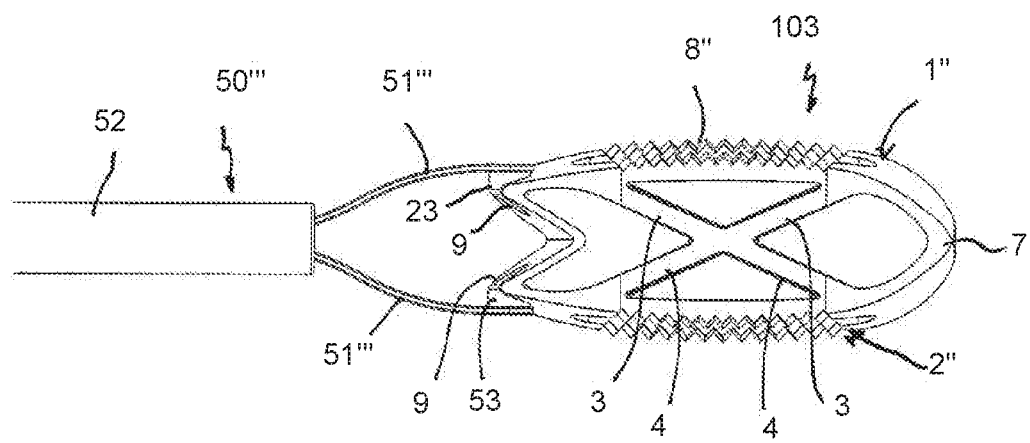
FIG. 38 shows a front view of the implant and a side view of the instrument of FIG. 37 engaging the implant.

Referring to FIGS. 35 to 40, a third aspect of the attachment of an instrument to the intervertebral implant is illustrated. An intervertebral implant 103 is similar to the intervertebral implant 100''' shown in FIGS. 23 to 24 except a specifically formed sidewall 7''' at one of the ends that connects the upper wall 1'' and the lower wall 2''. The sidewall 7''' has a V-shaped contour with the tip of the V-shape oriented towards the center of the implant. At the outermost ends in each of the sidewall portions that form the connection to the upper wall 1'' and the lower wall 2'' a cylinder segment-shaped recess 9 is provided that serves as an engagement portion for an instrument. The cylinder segment-shaped recess 9 has such a size that cylindrical projections of an instrument can engage the recess from above and below and once engaged, cannot be removed laterally. A cylinder axis is substantially perpendicular to the upper wall 1'' and to the lower wall 2''. An instrument 50''' comprises two arms 51''' that are guided in a sleeve 52. The sleeve 52 is displaceable relative to the arms 51'''. The arms 51''' can be, for example, shaped as flat bars that are slightly convexly curved in a region near their free ends and that comprise cylindrical projections 53 fitting into the cylinder segment-shaped recesses 9. The arms 51''' extend out of the sleeve 52 in such a manner that in an opened position the distance between the cylindrical projections 53 is greater than the distance of the cylinder segment-shaped recesses 9 in the height direction. Furthermore, the arms 51''' are configured to be elastically movable towards each other when the sleeve 52 is displaced relative to the arms 51''' in the direction of the free ends of the arms 51'''. Hence, the arms 51''' can assume a closed position as depicted in FIGS. 37 and 38 where the cylindrical projections 53 engage the recesses 9 and thereby the implant 103 is held by the instrument 50'''. The cylindrical projections 53 and the recesses 9 form a pivot joint that allows to pivot the implant 103 relative to the instrument 50''' around an axis defined by the cylindrical recesses 9 and the projections 53.

Figure 39:
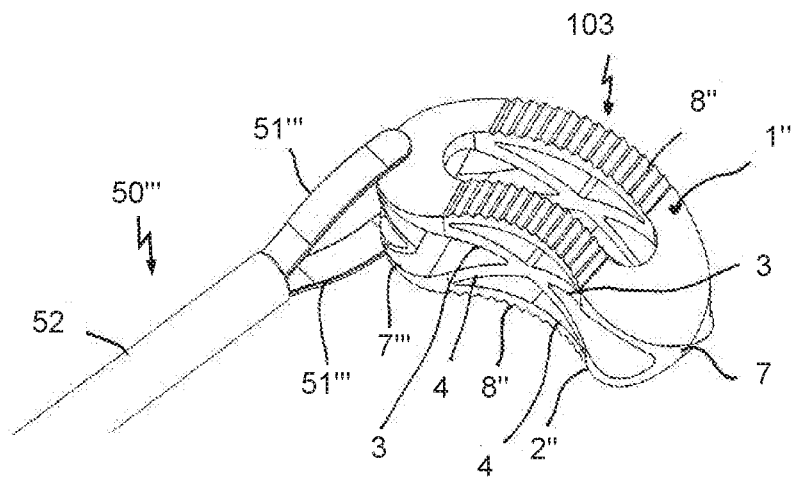
FIG. 39 shows a perspective view of the implant and the instrument according to FIGS. 35 to 38 rotated with respect to each other.
Figure 40:
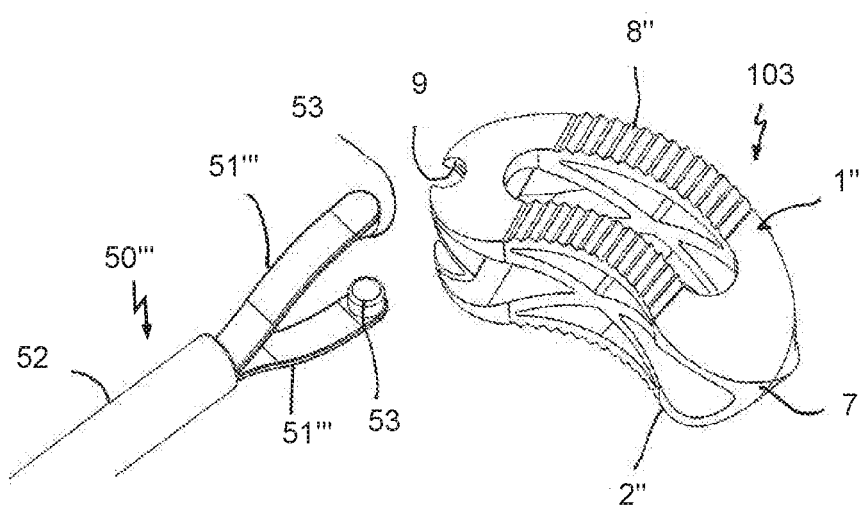
FIG. 40 shows a perspective view of the implant and the instrument of FIG. 39 wherein the implant is released from the instrument.

In use, first, the arms 51''' are in an opened position as depicted in FIGS. 35 and 36, and moved towards the implant 103. By displacing the sleeve 52 relative to the arms 51''' in the direction of the free end of the arms 51''', the cylindrical projections 53 engage the recesses 9 as depicted in FIGS. 37 and 38. The arms are in the closed position and hold the implant. In the closed position the implant can be rotated relative to the instrument so that the implant can be inserted along a curved trajectory as depicted in FIG. 39. After placement of the implant 103, the sleeve 52 is retracted and the arms move into the opened position, thereby releasing the implant 103. It shall be noted, that the intervertebral implant can have any design according to the previous described embodiments. However, to facilitate the insertion, it might be advantageous to have a sidewall in which the pivot joint can be established.

Figure 41:
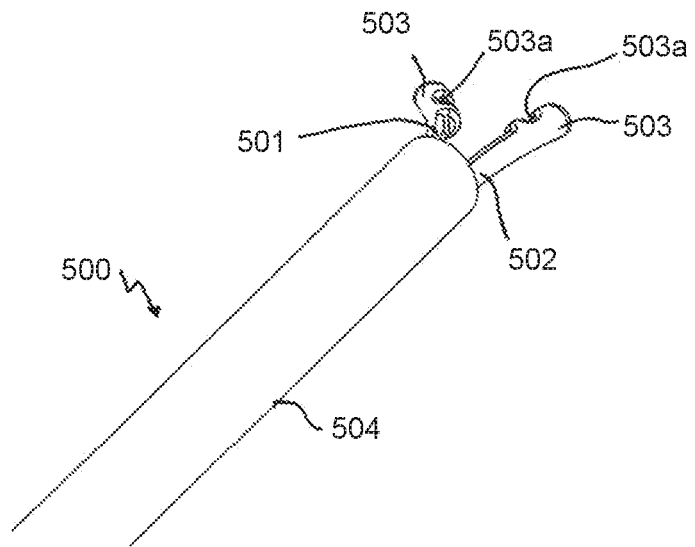
FIG. 41 shows a perspective view of a further embodiment of the instrument.
Figure 42A:
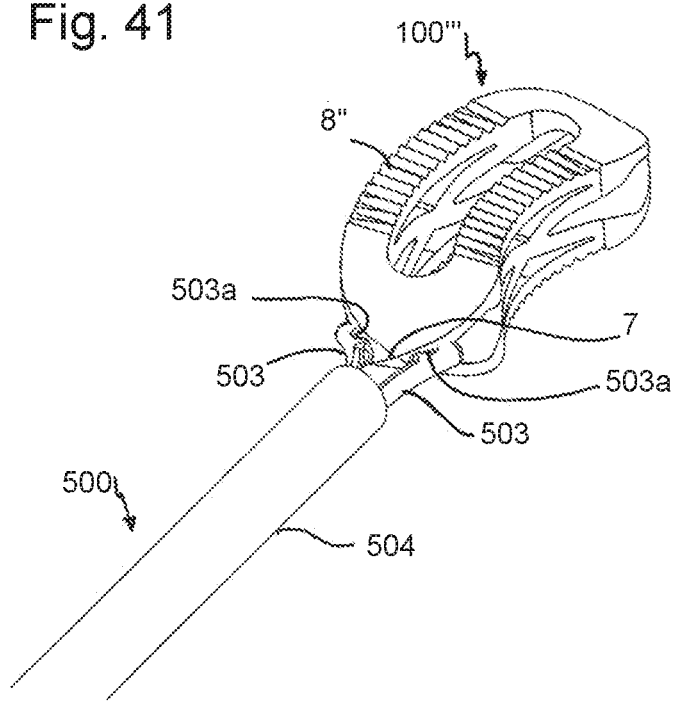
FIG. 42A to 42C show perspective views of steps of engaging and moving the intervertebral implant with the instrument of FIG. 41 to the implantation site and releasing the implant after placement.
Figure 42B:
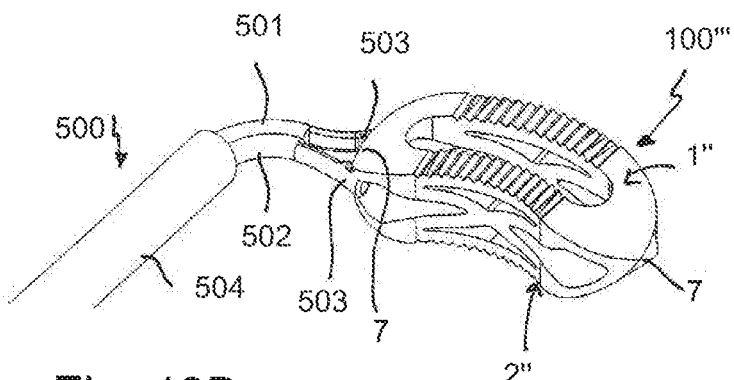
Figure 42C:
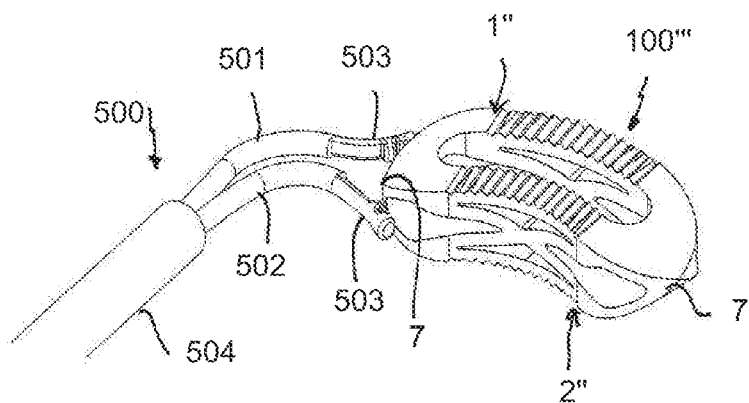
Figure 42D:
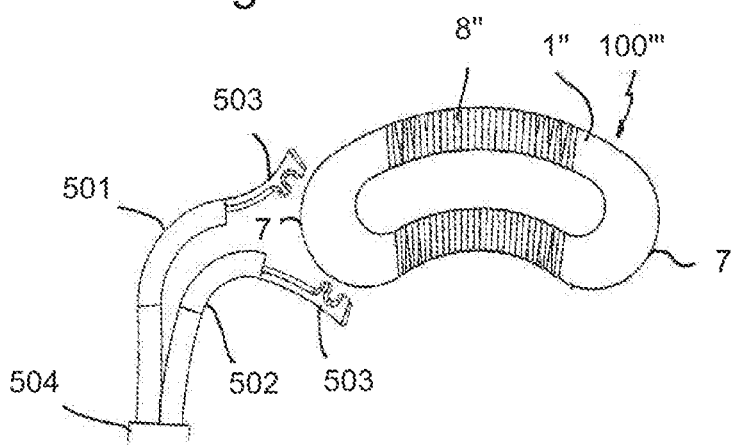
FIG. 42D shows a top view of the implant and the instrument as depicted in FIG. 42C.

A fourth aspect of the attachment of an instrument to the implant will be described with reference to FIGS. 41 to 42d. As illustrated in FIG. 42a, the implant may be shaped identical or similar to the implant 100''' as described with reference to FIGS. 23 and 24. However, any other implant design may also be used in connection with the instrument. Referring to FIG. 41, the instrument 500 comprises two arms 501, 502 with engagement portions 503 at the free end of each of the arms for engaging the implant 100'''. The engagement portions 503 comprise recesses or projections or hook-like portions that are configured to hold a portion of the intervertebral implant. In an embodiment, as shown in FIG. 42a, the engagement portions 503 have two opposed recesses 503a that engage a portion of the sidewall 7 of the implant. The arms 501, 502 are formed as wires and have a certain flexibility. In particular, the wires can be made of nickel titanium alloy and can have super-elastic properties at least in the temperature range that occurs during insertion of the implant. This permits to easily bend the arms during insertion of the implant. The arms 501, 502 are guided in a sleeve 504 and can be displaced relative to the sleeve 504 so that the arms can protrude out of the sleeve at different length. To permit the advancement of the implant 100''' along a curved trajectory during insertion, one arm 501 acts as a pressure arm and the other arm 502 acts as a tension arm. At a rear end of the instrument (not shown), the arms may be connected via a hand wheel that allows to move the pressure arm 501 further out of the sleeve 504 and to simultaneously retract the tension arm 502. As depicted in FIGS. 42a to 42b, after engagement of the implant with the engagement portions 503, by actuating the arms, the implant 100''' can be moved along a curved trajectory relative to the sleeve 504. Thereafter, moving both arms further outward of the sleeve 504 releases the vertebral implant 100''' from the engagement portions 503 as depicted in FIGS. 42c and 42d.

Figure 43:
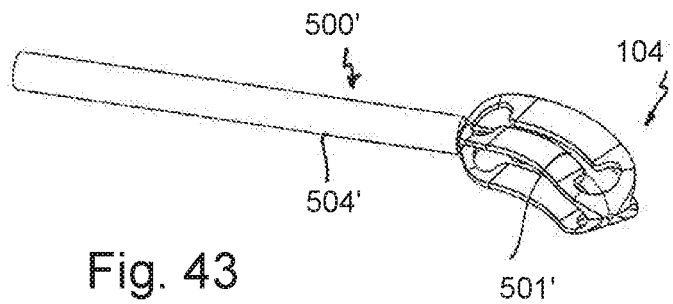
FIG. 43 shows a perspective view of a still further embodiment of the instrument attached to an intervertebral implant in a first position.
Figure 44:
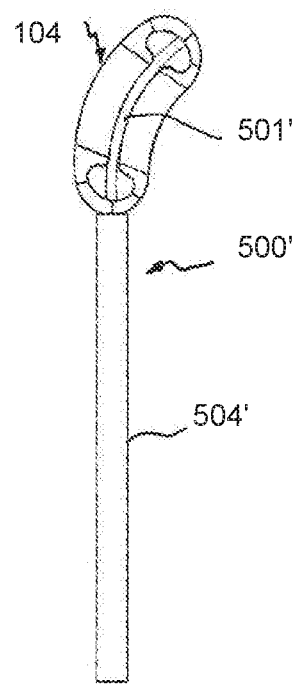
FIG. 44 shows a top view of the instrument and the intervertebral implant depicted in FIG. 43.
Figure 45:
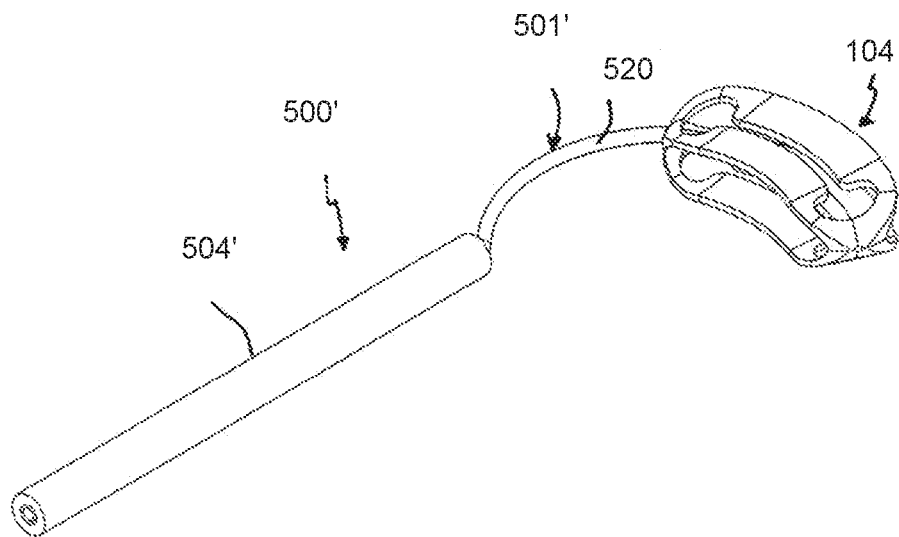
FIG. 45 shows a perspective view of the implant and the instrument depicted in FIG. 43 in a second position.
Figure 46:
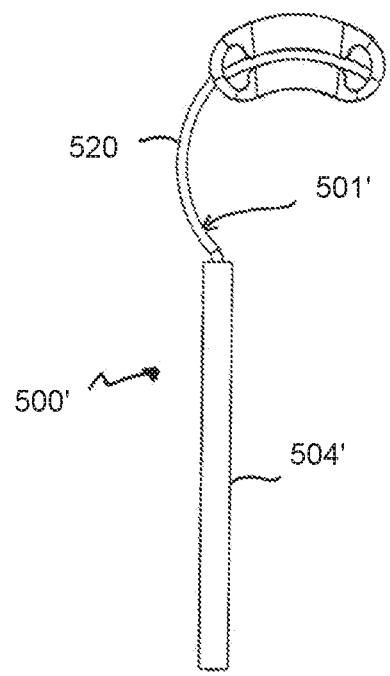
FIG. 46 shows a top view of the implant and the instrument depicted in FIG. 45.

A further embodiment of using an instrument comprising super-elastic nickel titanium wires is explained with reference to FIGS. 43 to 46. An intervertebral implant 104 is shown only schematically with an upper wall 1 and a lower wall 2 and sidewalls 7, a slot 5 but with the load transmitting part consisting of the arms 3 and the legs 4 being omitted. An instrument 500' comprises a sleeve 504' and one implant engagement member 501' in the form of a nickel titanium wire having superelastic and shape memory properties. The wire is guided through the implant 104 in the lengthwise direction. Preferably, the wire has a curved portion 520 wherein the curvature is permanently memorized by the wire. The curved portion 520 is straightened when it is accommodated in the sleeve 504' during preparation of the instrument with the implant before insertion as depicted in FIGS. 43 and 44. To insert the implant, the wire 501' is moved further outward from the sleeves 504' so that the portion 520 automatically assumes the curved shape. Thereby, the intervertebral implant 104 can be inserted along a curved trajectory. Once the intervertebral implant has been placed in the intervertebral space and contacts the vertebral endplates, it is held by the adjacent vertebral bodies and the instrument can be removed by pulling the wire 501' further back into the sleeve 504'.

Figure 47:
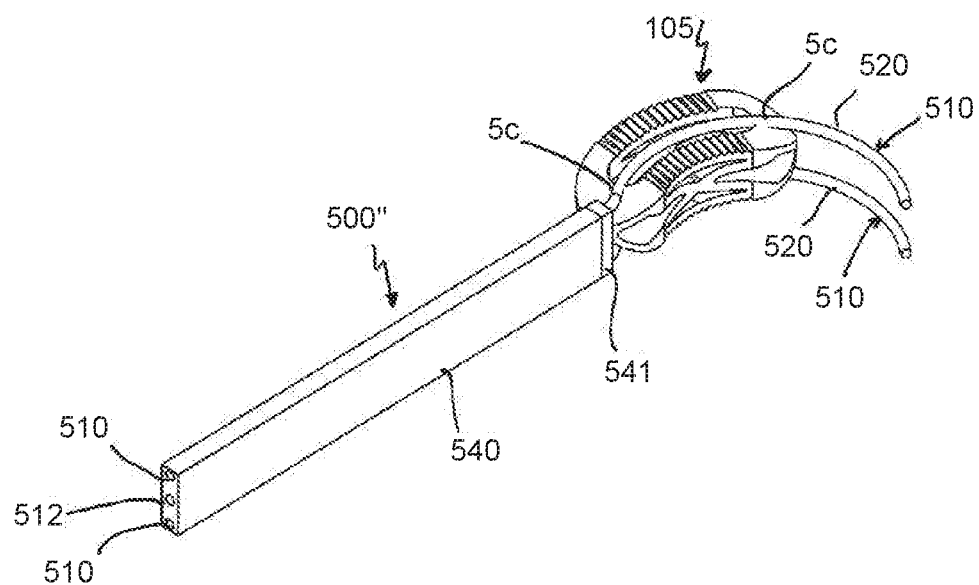
FIG. 47 shows a perspective view of a still further embodiment of the instrument attached to an implant in a first position.
Figure 48:
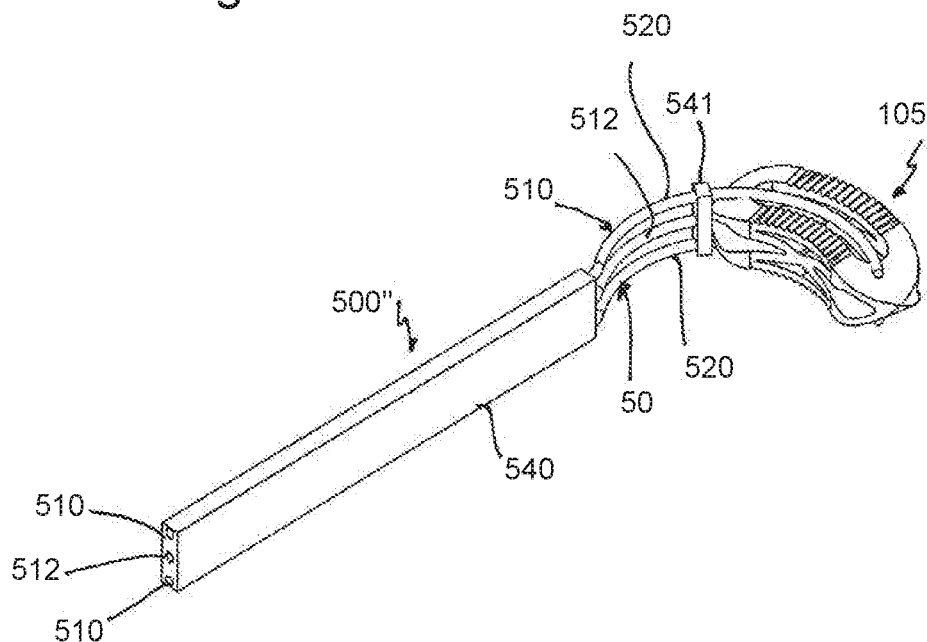
FIG. 48 shows a perspective view of the instrument and the implant of FIG. 47 in a second position.
Figure 49:
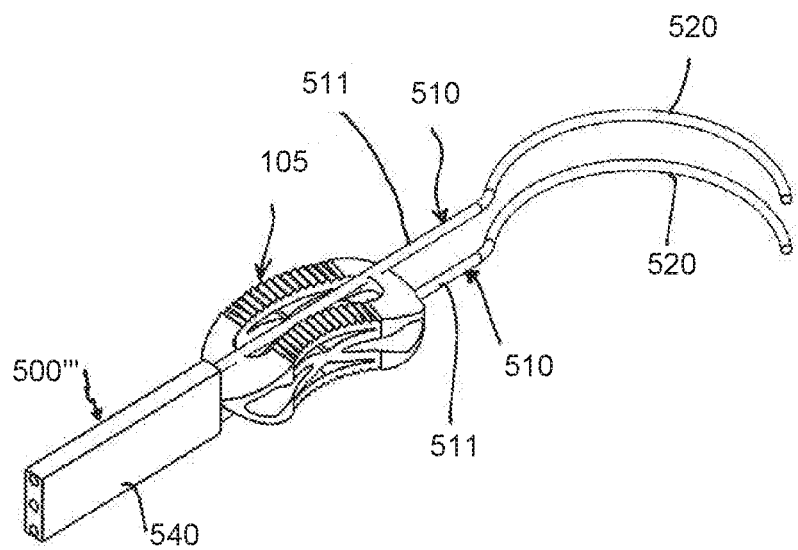
FIG. 49 shows a perspective view of a modified instrument and the implant of FIG. 47.
Figure 50:
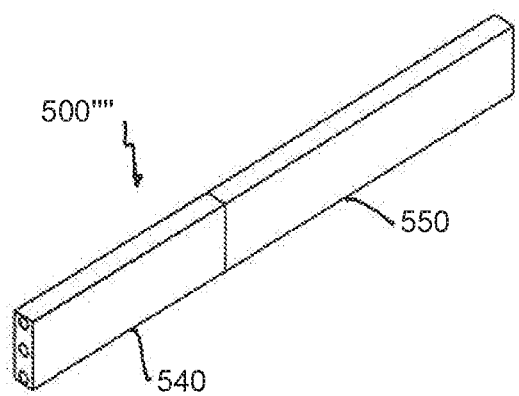
FIG. 50 shows a perspective view of a further modification of the instrument depicted in FIG. 47 to FIG. 49.

A fifth aspect of the attachment of the intervertebral implant to an instrument will described with reference to FIGS. 47 to 50. An intervertebral implant 105 depicted in FIG. 47 to 49 is similar to the intervertebral implant as depicted in FIGS. 23 and 24. Additionally, on the upper wall 1" and the lower wall 2" recesses 5c are provided for guiding implant engagement members therethrough. The implant engagement members are formed as nickel titanium wires 510 that are fixed in a holder 540 of an instrument 500" and that have curved portions 520 adjacent to the free ends. The curved portions 520 extend out of the holder 540. As shown in FIG. 47, a movable sleeve 541 is provided at the end of the holder 540 that is closer to the free ends of the wires 510. The movable sleeve 541 is slidable with respect to the wires 510 and is fixedly connected to a third wire 512 that is guided in the holder 540 and that can be pushed or pulled manually.

First, the intervertebral implant 105 is inserted between the wires 510 close to the movable sleeve 541 and held in this position. Then, the third wire 512 is pushed more outward of the holder 540, thereby moving the sleeve 541. The sleeve 541 pushes the implant 105 along the curved portions 520 of the wires 510 so that the wires 510 act as rails to advance the implant 105 along a curved trajectory. While two wires 510 are shown, it shall be understood that only one wire 510 may be sufficient. The sleeve 541 also prevents spreading of the wires 510 in the height direction so that the wires 510 remain in the recesses 5c of the implant 105.

As illustrated in FIG. 49, an instrument 500''' also can have wires 510 wherein straight portions 511 protrude out of the holder 540 to some extent which allows to move the implant 105 first along a straight trajectory and then along a curved trajectory.

An instrument 500'''' may be delivered with the holder 540 and a protective cap 550, wherein in the holder 540 the wires 510 are fixed and wherein the curved portion 520 are straightened in the protective cap 550. Once the protective cap 550 is removed, the wires can assume their curved shape 520 due to the shape memory effect of the material.

Figure 51:
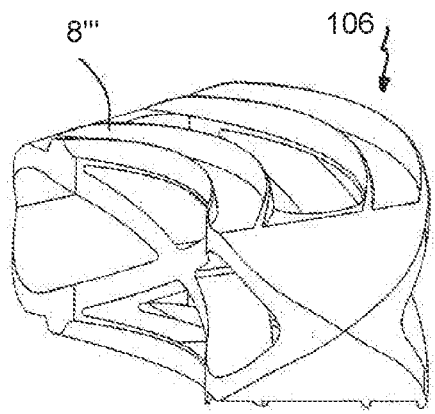
FIG. 51 shows a perspective view of an intervertebral implant according to a still further embodiment.
Figure 52:
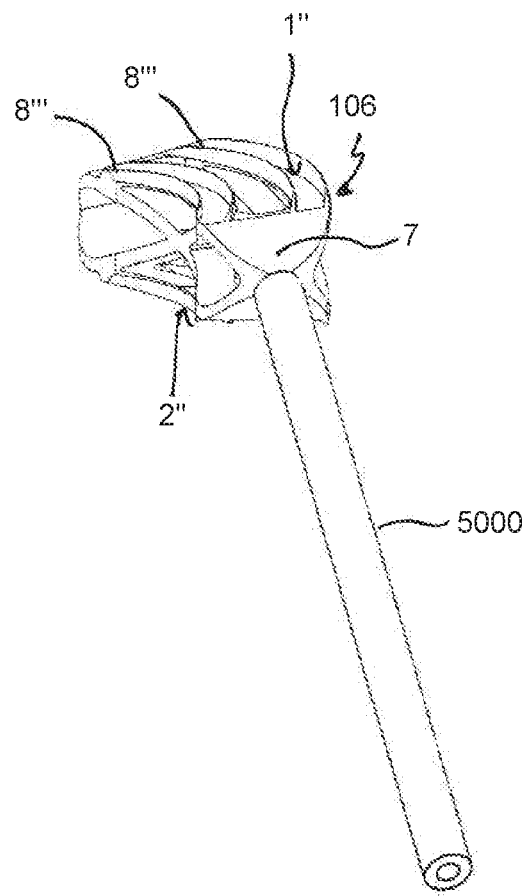
FIG. 52 shows a perspective view of the intervertebral implant of FIG. 51 with a still further instrument attached thereto.

A sixth aspect of an attachment of the intervertebral implant to an instrument will be explained with reference to FIGS. 51 and 52. An intervertebral implant 106 according to FIG. 51 has a curved contour and keel-shaped teeth 8''' that are arranged in rows wherein each row extends along the direction of insertion, i.e. in the lengthwise direction. The implant 106 comprises the top wall 1, bottom wall 2 and sidewalls 7. In one of the sidewalls a connection structure (not shown) is provided that allows to attach an insertion instrument 5000. Such a connection structure may be a threaded hole and the instrument 5000 may have a corresponding threaded projection. After the instrument 5000 has been attached to the intervertebral implant 106 the intervertebral implant can be first inserted by pushing it with the instrument 500''' along a straight trajectory. As soon as the intervertebral implant 106 enters the intervertebral space the keel-like teeth 8''' engage the upper and lower end plates and guide the implant 106 along a curved trajectory to the final position.

Figure 53:
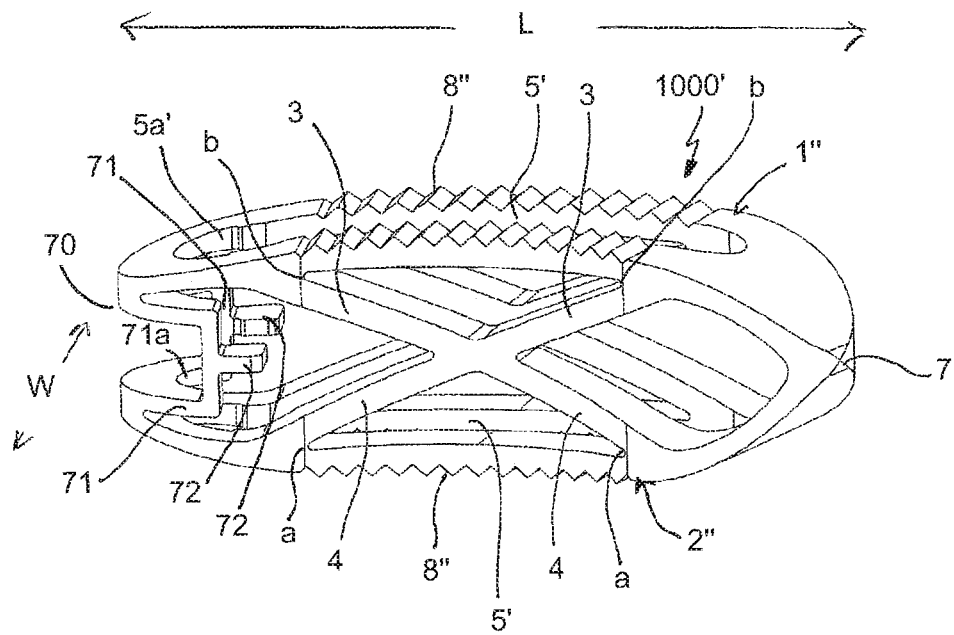
FIG. 53 shows a perspective view of a further embodiment of an intervertebral implant.
Figure 54:
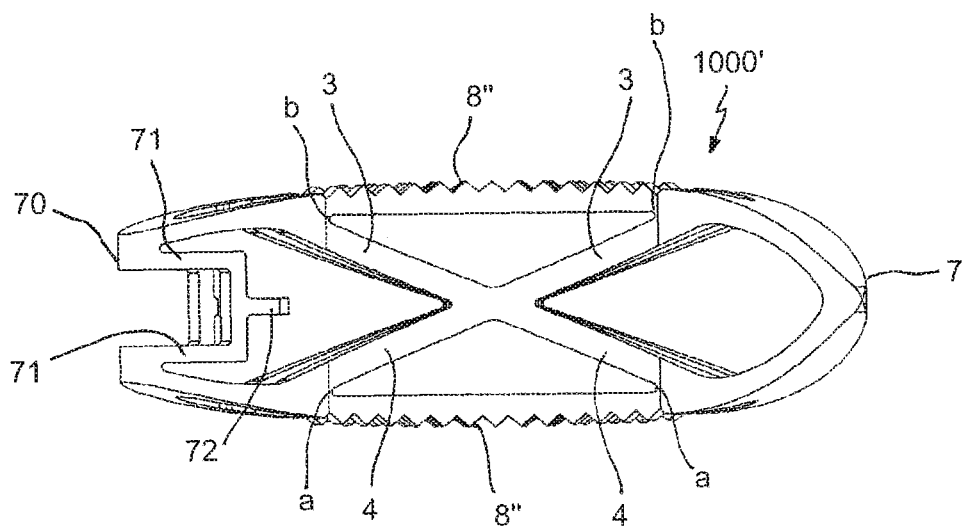
FIG. 54 shows a front view of the intervertebral implant of FIG. 53.

A seventh aspect of an attachment of the intervertebral implant to an instrument will be explained with reference to FIGS. 53 to 60A to 60D. An intervertebral implant 1000' according to FIGS. 53 and 54 is similar to the intervertebral implant 100''' of FIGS. 23 and 24. Parts and portions that are identical or highly similar to those of FIGS. 23 and 24 are indicated with the same reference numerals and the description thereof is not repeated. A sidewall 70 comprises a structure that is configured to receive an insert member that permits engagement with an instrument. The sidewall 70 comprises two sidewall portions 71 that extend towards the inside of the intervertebral implant with an outer contour corresponding to the outer contour of the upper wall 1″ and the lower wall 2″ and that are separated in the widthwise direction from each other by the through-slot 5′. In a front view of the implant 1000′, as depicted in FIG. 54, and similarly in a rear view, the sidewall portions 71 connect the upper wall 1″ and the lower wall 2″ in a substantially rectangular manner. Two substantially horizontal projections 72 extend from the innermost portion of the sidewall portions 71 with their free ends directed towards the inside of the intervertebral implant, more specifically towards the opposite sidewall 7. The horizontal projections 72 have a substantially rectangular cross-section. The projections 72 are also separated from each other by the through-slot 5′. At the end of the sidewall 70, the width of the through-slot 5′ has a slightly enlarged end portion 5a′. The structure of the sidewall 70 serves for accommodating an insert member 700 that permits to couple an instrument to the intervertebral implant 1000′. An end of the through-slot 5′ may form a portion 71a of the sidewall 70 that provides an abutment for the insert member 700.

Figure 55:
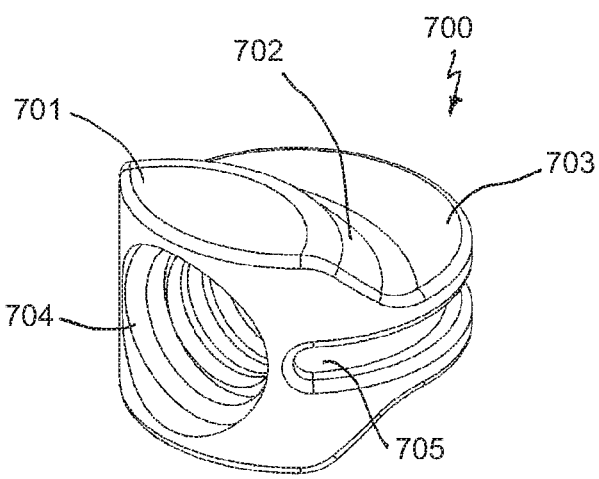
FIG. 55 shows a perspective view of an insert member for coupling the intervertebral implant of FIGS. 53 and 54 to an instrument.
Figure 56:
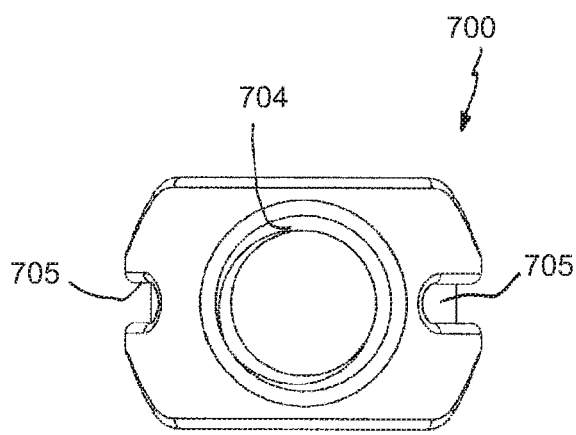
FIG. 56 shows a side view of the insert member of FIG. 55.
Figure 57:
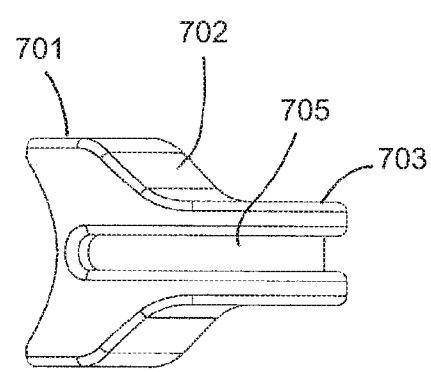
FIG. 57 shows a front view of the insert member of FIGS. 55 and 56.
Figure 58:
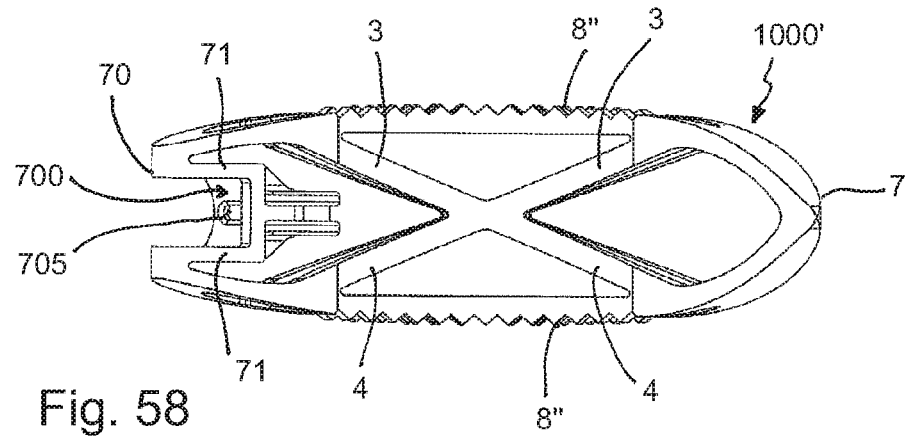
FIG. 58 shows a front view of the intervertebral implant of FIGS. 53 and 54 with the insert member of FIGS. 55 to 57.
Figure 59:
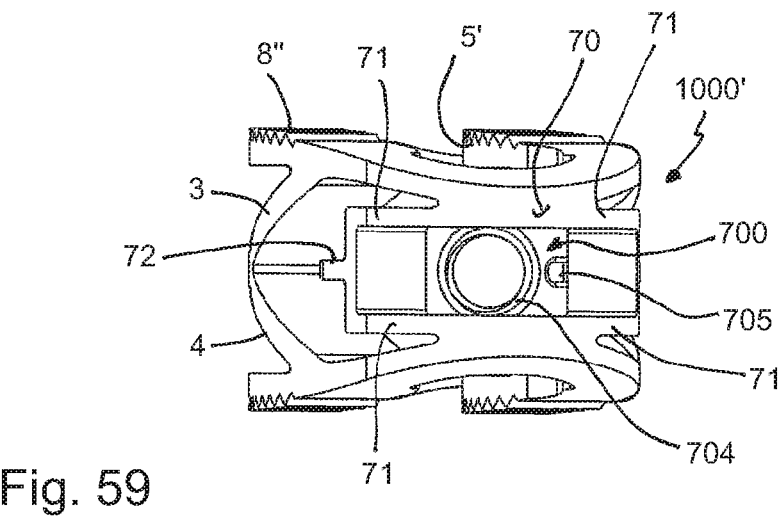
FIG. 59 shows a side view of the intervertebral implant with the insert member of FIG. 58.
Figure 60:
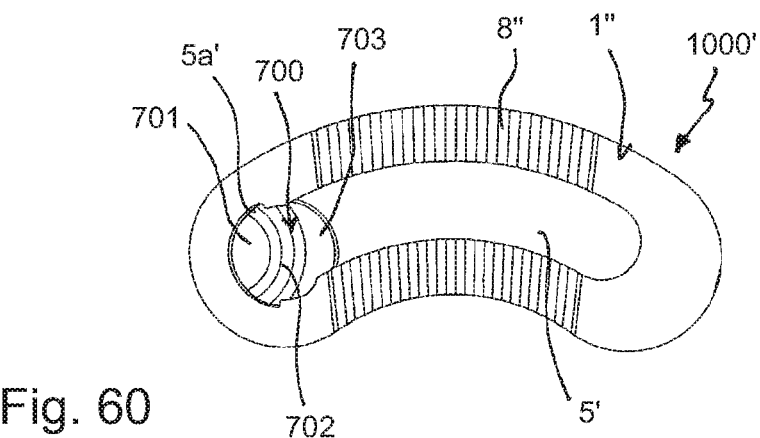
FIG. 60 shows a top view of the intervertebral implant with the insert member of FIGS. 58 and 59.

As depicted in FIGS. 55 to 57, the insert member 700 is a substantially cylindrical part that comprises a front portion 701 with a first height, a rear portion 703 with a second height smaller than the first height and a middle portion 702 with a height decreasing from the front portion 701 towards the rear portion 703. The first height of the front portion 701 is smaller than the distance between the upper wall 1″ and the lower wall 2″ in a vertical or height-direction. The top and bottom surfaces of the front portion 701 and the rear portion 703 of the insert member 700 are substantially flat. In a width-direction the front portion 701 of the insert member 700 is smaller than a total width of the sidewall 70 of the intervertebral implant 1000′, as shown in FIG. 59. At the center of the front portion 701 in a side view, as depicted in FIG. 56, a horizontally extending threaded hole 704 is provided that is configured to be engaged with an instrument. Furthermore, a horizontally extending slot 705 is provided that extends from the rear portion 703 up to a distance at each side of the threaded hole 704. The slot 705 is configured to be engaged by the horizontal projections 72 of the sidewall 70 of the intervertebral implant 1000′ from both sides.

The insert member 700 is inserted into the intervertebral implant 1000′ through the enlarged end portion 5a′ of the through-slot 5′. The rear portion 703 extends behind the rectangular sidewall portions 71 into the inside of the intervertebral implant 1000′. There, the horizontal projections 72 can engage the horizontal slot 705 when the insert member 700 is rotated. Once inserted, the insert member 700 can abut with its front portion 701 against the abutment 71a (see FIG. 53) and is prevented from falling out.

Figure 61A:
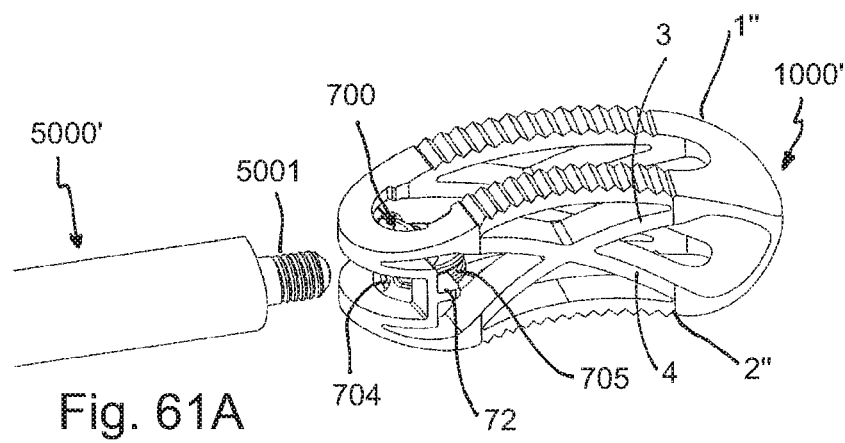
FIGS. 61A to 61D show steps of coupling an instrument to the intervertebral implant of FIGS. 53 to 60, of moving the intervertebral implant relative to the instrument and of decoupling the instrument from the intervertebral implant.
Figure 61B:
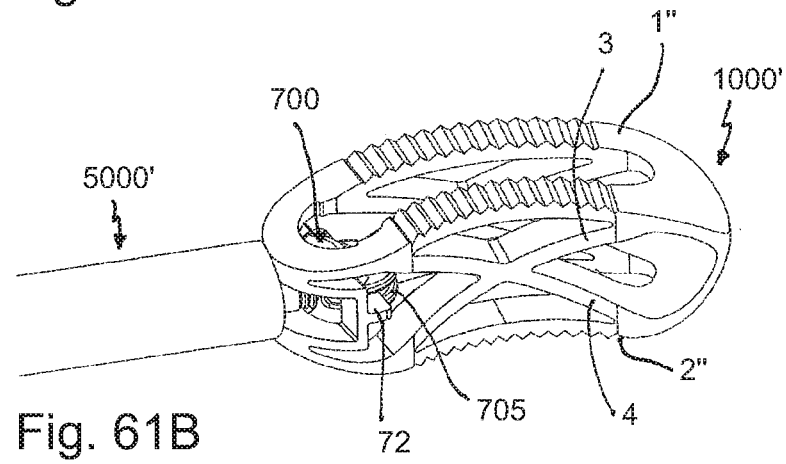
Figure 61C:
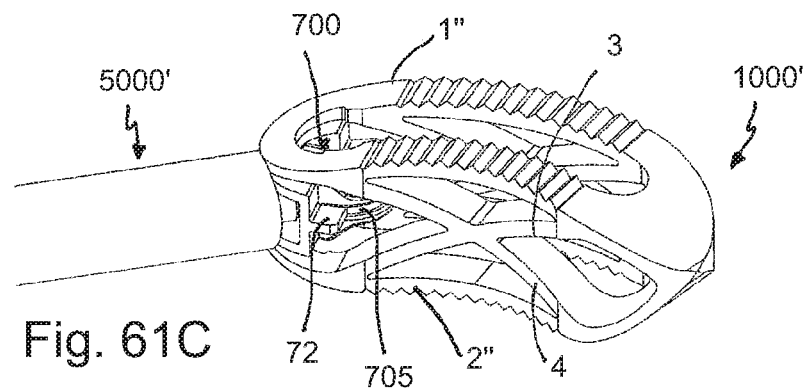
Figure 61D:
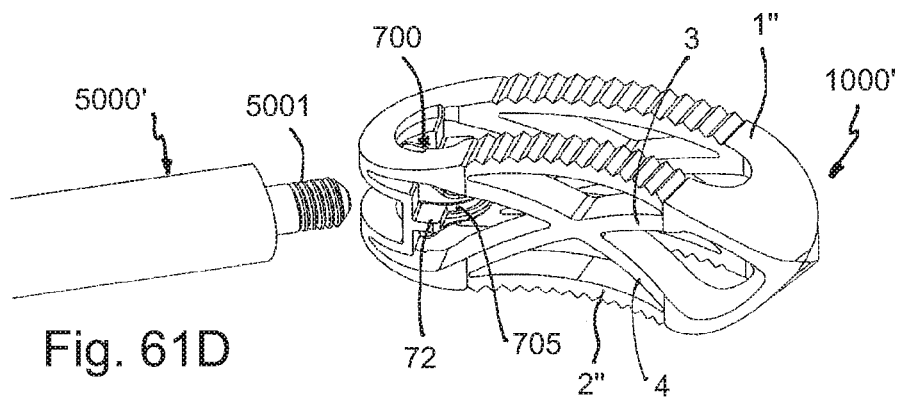

As illustrated in FIG. 61A, an instrument 5000′ comprises a threaded pin-like projection 5001 configured to engage the threaded hole 704 of the insert member 700. The instrument 5000′ may have, for example, a cylindrical, rod-like shape. As depicted in FIG. 61B, the intervertebral implant 1000′ is coupled to the instrument 5000′ by screwing the threaded pin-like projection 5001 into the threaded hole 704 of the insert member. Thereafter, as shown in FIG. 61C, the cylindrical insert member 700 can be rotated in a limited angular range relative to the intervertebral implant 1000′ by rotating the instrument 5000′. This permits to insert the intervertebral implant along a curved trajectory between the vertebral bodies. During rotation, the insert is held and guided by the projections 72. Finally, as shown in FIG. 61D, the instrument 5000′ can be decoupled by screwing the threaded pin-like projection 5001 out of the insert member 700.

Modifications of the above described embodiments and aspects of the attachment of an instrument to the intervertebral implant may be contemplated. For example, instead of a nickel titanium alloy as a material for the intervertebral implant, other shape memory alloys or shape memory polymers (SMPs) can be used. Such shape memory polymers may include linear block copolymers, for example shape memory polyurethane, thermoplastic polymers, for example polynorbornene, or chemically cross-linked SMP. The recovery level is then defined as the temperature at which the material has transformed to the high temperature structure.

The load transmitting part can be formed in a modified manner. For example, the connecting location c needs not to be in the middle between the upper wall and the lower wall in the height direction. The arms can have a length different from a length of the legs. The load transmitting parts needs not to be symmetric, for example one arm or leg can have a length different from a length of the other arm or leg, respectively.

It shall be noted that features of the embodiments described above can be combined with features of other embodiments, mixed and matched to produce a variety of further embodiments.

The invention claimed is:

1. A system comprising:
   an intervertebral implant comprising:
   an upper wall configured to engage a first vertebral end plate;
   a lower wall configured to engage a second vertebral end plate, wherein a central axis extends through the upper wall and the lower wall, and wherein the implant has a length and a width in respective directions perpendicular to the central axis, the length of the implant being greater than the width of the implant;
   an axially compressible load transmitting part extending between the upper wall and the lower wall and configured to transmit load between the upper wall and the lower wall, wherein the load transmitting part is attached to the upper wall at at least two first connecting locations, is attached to the lower wall at at least two second connecting locations, and has an X-shaped profile with the X-shape being viewable in a widthwise direction along which the width of the implant extends; and
   two sidewalls on opposite sides of the implant, wherein each sidewall extends between at least one of the first connecting locations and at least one of the second connecting locations and is distinct from the load transmitting part, each sidewall having at least a portion that is located at a same axial height as an axially compressible region of the load transmitting part while also being positioned farther away from the central axis than the entire upper wall, the entire lower wall, and the load transmitting part in a lengthwise direction along which the length of the implant extends;
   wherein at least one of the upper wall or the lower wall is convexly curved, wherein a plurality of bone engagement projections are formed on the at least one of the upper wall or the lower wall, and wherein all of the bone engagement projections are located between the connecting locations of the load transmitting part and project farther axially than all portions of the implant that include or that are located outside of the connecting locations toward the sidewalls, with at least one of the plurality of projections approximate the central axis defining a greatest axial height of the implant measured between the upper and lower walls;
wherein the load transmitting part is configured to assume a compressed condition in which the greatest axial height of the implant is a first height, and an expanded condition in which the greatest axial height of the implant is a second height greater than the first height; and
wherein the implant is made of a material that exhibits shape memory properties that permit the implant to remain in the compressed condition without outside forces acting upon it and to change to the expanded condition in response to a temperature being at a recovery level; and
an instrument for inserting the intervertebral implant, wherein the instrument is configured to engage the implant in the compressed condition without compressing the implant, and to release the implant after insertion.

2. The system of claim 1, wherein when the load transmitting part assumes the expanded condition, the X-shape is configured to transmit load between the upper wall and the lower wall.

3. The system of claim 1, wherein the recovery level of the temperature is in the range of 20° C. to 35° C.

4. The system of claim 3, wherein the recovery level of the temperature is in the range of 25° C. to 30° C.

5. The system of claim 1, wherein the implant is self-expandable when exposed to body temperature.

6. The system of claim 1, wherein the material is a nickel titanium alloy with a nickel content of 50 to 52 atomic percent nickel.

7. The system of claim 6, wherein the nickel content is 50.6 to 51.0 atomic percent nickel.

8. The system of claim 1, wherein the load transmitting part comprises two arms that are attached to the upper wall at the first connecting locations and two legs that are attached to the lower wall at the second connecting locations, wherein the two arms and the two legs are connected together at a third connecting location between the upper wall and the lower wall, and wherein in the expanded condition a second angle that is enclosed by the two arms is greater than a first angle enclosed between one of the arms and one of the legs.

9. The system of claim 8, wherein the second angle is between 100° and 150°, and wherein a sum of the second angle and the first angle is 180°.

10. The system of claim 1, wherein the first height of the implant in the compressed condition is equal to or less than 85% of the second height of the implant in the expanded condition.

11. The system of claim 10, wherein the first height of the implant in the compressed condition is equal to or less than 75% of the second height of the implant in the expanded condition.

12. The system of claim 1, wherein the bone engagement projections are provided only within an area between the connecting locations of the load transmitting part.

13. The system of claim 1, wherein a slot extends in the lengthwise direction through the implant from the upper wall to the lower wall.

14. The system of claim 1, wherein the implant is coated.

15. The system of claim 1, wherein the instrument comprises a sleeve and at least one wire guidable through the sleeve, wherein the wire is configured to engage the implant and to be actuated to guide the implant for inserting the implant.

16. The system of claim 1, wherein the implant further comprises an engagement portion located at a first axial height on the implant, and wherein when the implant changes from the compressed condition to the expanded condition, a first part of the axially compressible region of the load transmitting part expands away from the first axial height in a first axial direction and a second part of the axially compressible region expands away from the first axial height in a direction opposite the first axial direction, and wherein the instrument is configured to engage the engagement portion of the implant in the compressed condition without compressing the implant, and to release the implant after insertion.

17. The system of claim 16, wherein when the instrument engages the engagement portion of the implant in the compressed condition, the instrument extends laterally away from the implant along a central axis of the instrument that is located at a same axial height as the axially compressible region of the load transmitting part.

18. The system of claim 1, wherein the load transmitting part is integrally attached to the upper wall at the at least two first connecting locations and is integrally attached to the lower wall at the at least two second connecting locations.

19. The system of claim 1, wherein a slot extends axially from the upper wall to the lower wall and completely separates the load transmitting part into two parts that are spaced apart from one another in the widthwise direction.

20. The system of claim 19, wherein the implant further comprises an engagement portion configured to engage the instrument, and wherein the engagement portion extends in the lengthwise direction past an outermost end of the slot towards the central axis.

21. The system of claim 19, wherein a space defined between the load transmitting part and one of the sidewalls extends outwardly past an outermost end of the slot in the lengthwise direction.

22. The system of claim 1, wherein the implant further comprises an engagement portion configured to engage the instrument, with an opening for accessing the engagement portion having a width measured in a direction transverse to the central axis that is greater than a height measured in a direction parallel to the central axis.

23. A method of inserting an intervertebral implant between vertebrae using an instrument, the intervertebral implant comprising an upper wall configured to engage a first vertebral end plate, a lower wall configured to engage a second vertebral end plate, wherein a central axis extends through the upper wall and the lower wall, and wherein the implant has a length and a width in respective directions perpendicular to the central axis, the length of the implant being greater than the width of the implant, an axially compressible load transmitting part extending between the upper wall and the lower wall and configured to transmit load between the upper wall and the lower wall, wherein the load transmitting part is attached to the upper wall at at least two first connecting locations, is attached to the lower wall at at least two second connecting locations, and has an X-shaped profile, with the X-shape being viewable in a widthwise direction along which the width of the implant extends, and two sidewalls on opposite sides of the implant, wherein each sidewall extends between at least one of the first connecting locations and at least one of the second connecting locations and is distinct from the load transmitting part, each sidewall having at least a portion that is located at a same axial height as an axially compressible region of the load transmitting part while also being positioned farther away from the central axis than the entire upper wall, the entire lower wall, and the load transmitting part in a lengthwise direction along which the length of the implant extends, wherein at least one of the upper wall or the lower wall is convexly curved, wherein a plurality of bone engagement projections are formed on the at least one of the upper wall or the lower wall, wherein all of the bone engagement projections are located between the connecting locations of the load transmitting part and project farther axially than all portions of the implant that include or that are located outside of the connecting locations toward the sidewalls, with at least one of the plurality of projections approximate the central axis defining a greatest axial height of the implant measured between the upper and lower walls, wherein the load transmitting part is configured to assume a compressed condition in which the greatest axial height of the implant is a first height, and an expanded condition in which the greatest axial height of the implant is a second height greater than the first height, and wherein the implant is made of a material that exhibits shape memory properties that permit the implant to remain in the compressed condition without outside forces acting upon it and to change to the expanded condition in response to a temperature being at a recovery level, the method comprising:

engaging the implant with an instrument when the implant is in the compressed condition without compressing the implant;

inserting the implant between vertebrae using the instrument; and releasing the implant after insertion between the vertebrae.

24. The method of claim 23, wherein engaging the implant comprises:

guiding at least one wire of the instrument through a sleeve of the instrument;

engaging the implant with the at least one wire; and guiding the implant using the at least one wire.

\* \* \* \* \*